(12) United States Patent
VanTassel et al.

(10) Patent No.: US 6,652,555 B1
(45) Date of Patent: Nov. 25, 2003

(54) BARRIER DEVICE FOR COVERING THE OSTIUM OF LEFT ATRIAL APPENDAGE

(75) Inventors: Robert A. VanTassel, Excelsior, MN (US); Robert G. Hauser, Long Lake, MN (US); Robert Schwartz, Rochester, MN (US); David Holmes, Rochester, MN (US); Gregg S. Sutton, Maple Grove, MN (US); Thomas E. Borillo, Plymouth, MN (US); Jeffrey Welch, New Hope, MN (US)

(73) Assignee: Atritech, Inc., Minneapolis, MN (US)

( * ) Notice: Subject to any disclaimer, the term of this patent is extended or adjusted under 35 U.S.C. 154(b) by 256 days.

(21) Appl. No.: 09/642,291

(22) Filed: Aug. 18, 2000

Related U.S. Application Data

(63) Continuation-in-part of application No. 09/614,091, filed on Jul. 11, 2000, which is a continuation-in-part of application No. 09/428,008, filed on Oct. 27, 1999.
(60) Provisional application No. 60/196,454, filed on Apr. 11, 2000, provisional application No. 60/206,967, filed on May 25, 2000, provisional application No. 60/209,511, filed on Jun. 5, 2000, provisional application No. 60/211,896, filed on Jun. 16, 2000, and provisional application No. 60/217,125, filed on Jul. 10, 2000.

(51) Int. Cl.$^7$ ............................................. A61M 29/00
(52) U.S. Cl. ..................... 606/200; 606/151; 623/23.7; 128/898
(58) Field of Search ........................... 606/200, 1, 151, 606/108, 193, 191; 623/1, 11.11, 23.7; 128/898

(56) References Cited

U.S. PATENT DOCUMENTS

| | | | |
|---|---|---|---|
| 178,283 A | 6/1876 | French | 604/109 |
| 1,967,318 A | 7/1934 | Monahan | 604/106 |
| 3,844,302 A | 10/1974 | Klein | 135/6 |
| 3,874,388 A | 4/1975 | King et al. | 606/232 |
| 4,007,743 A | 2/1977 | Blake | 606/232 |

(List continued on next page.)

FOREIGN PATENT DOCUMENTS

| | | | |
|---|---|---|---|
| WO | WO93/13712 | 7/1993 | A61B/17/00 |
| WO | WO 97/21402 | 6/1997 | |
| WO | WO 97/28749 | 8/1997 | A61B/17/068 |
| WO | WO 98/02100 | 1/1998 | A61B/17/12 |
| WO | WO 98/17187 | 4/1998 | A61B/17/36 |

(List continued on next page.)

OTHER PUBLICATIONS

Dotter, et al., "Transluminal Expandable Nitinol Coil Stent Grafting: Preliminary Report," *Radiology* vol. 147, No. 1, pp. 259–260, Apr. 1983.

(List continued on next page.)

*Primary Examiner*—Brian L. Casler
*Assistant Examiner*—Jeremy Thissell
(74) *Attorney, Agent, or Firm*—Fish & Neave; Robert R. Jackson; Michael J. Chasan

(57) ABSTRACT

A membrane applied to the ostium of an atrial appendage is disclosed. The membrane prevents blood clots in the atrial appendage from escaping therefrom and entering the blood stream which can result in a blocked blood vessel, leading to strokes and heart attacks. The membrane may be permeable or impermeable with respect to blood flow. The membrane is configured to extend over the ostium of the left atrial appendage. The membrane has an outer periphery with a dimension larger than a corresponding dimension of the ostium. Securement means is provided to secure the outer periphery of the membrane in direct engagement with the atrial wall surrounding the ostium. The securement means may located between the membrane and the atrial wall, or the securement means may extend distally from the membrane through the ostium.

8 Claims, 22 Drawing Sheets

U.S. PATENT DOCUMENTS

| | | | |
|---|---|---|---|
| 4,341,218 A | 7/1982 | Ü | 606/195 |
| 4,585,000 A | 4/1986 | Hershenson | 606/194 |
| 4,603,693 A | 8/1986 | Conta et al. | 227/179.1 |
| 4,665,906 A | 5/1987 | Jervis | 606/78 |
| 4,710,192 A | 12/1987 | Liotta et al. | 606/108 |
| 4,917,089 A | 4/1990 | Sideris | 606/215 |
| 4,921,484 A | 5/1990 | Hillstead | 604/104 |
| 5,041,090 A | 8/1991 | Scheglov et al. | 604/101.02 |
| 5,041,093 A | 8/1991 | Chu | 604/104 |
| 5,042,707 A | 8/1991 | Taheri | 606/213 |
| 5,053,009 A | 10/1991 | Herzberg | 604/104 |
| 5,064,435 A | 11/1991 | Porter | 623/23.7 |
| 5,078,736 A | 1/1992 | Behl | 623/1 |
| 5,108,420 A | 4/1992 | Marks | 606/213 |
| 5,171,259 A | 12/1992 | Inoue | 606/213 |
| 5,176,692 A | 1/1993 | Wilk et al. | 606/151 |
| 5,192,301 A | 3/1993 | Kamiya et al. | 606/213 |
| 5,256,146 A | 10/1993 | Ensminger et al. | 604/104 |
| 5,258,042 A | 11/1993 | Mehta | 600/36 |
| 5,284,488 A | 2/1994 | Sideris | 606/213 |
| 5,306,234 A | 4/1994 | Johnson | 604/49 |
| 5,334,217 A | 8/1994 | Das | 606/213 |
| 5,350,399 A | 9/1994 | Erlebacher et al. | 606/213 |
| 5,353,784 A | 10/1994 | Nady-Mohamed | 600/205 |
| 5,370,657 A | 12/1994 | Irie | 606/200 |
| 5,375,612 A | 12/1994 | Cottenceau et al. | 128/899 |
| 5,417,699 A | 5/1995 | Klein et al. | 606/144 |
| 5,421,832 A | 6/1995 | Lefebvre | 264/173.11 |
| 5,425,744 A | 6/1995 | Fagan et al. | 606/213 |
| 5,433,727 A | 7/1995 | Sideris | 606/213 |
| 5,443,454 A | 8/1995 | Tanabe et al. | 604/264 |
| 5,451,235 A | 9/1995 | Lock et al. | 606/213 |
| 5,464,408 A | 11/1995 | Duc | 606/108 |
| 5,469,867 A | 11/1995 | Schmitt | 128/898 |
| 5,490,856 A | 2/1996 | Person et al. | 606/139 |
| 5,522,822 A | 6/1996 | Phelps et al. | 606/151 |
| 5,522,836 A | 6/1996 | Palermo | 606/200 |
| 5,527,322 A | 6/1996 | Klein et al. | 606/144 |
| 5,527,338 A | 6/1996 | Purdy | 606/200 |
| 5,591,196 A | 1/1997 | Marin et al. | 606/198 |
| 5,614,204 A | 3/1997 | Cochrum | 424/423 |
| 5,634,936 A | 6/1997 | Linden et al. | 606/213 |
| 5,634,942 A | 6/1997 | Chevillon et al. | 623/1 |
| 5,637,097 A | 6/1997 | Yoon | 604/174 |
| 5,643,292 A | 7/1997 | Hart | 606/144 |
| 5,649,953 A | 7/1997 | Lefebvre | 606/200 |
| 5,662,671 A | 9/1997 | Barbut et al. | 606/170 |
| 5,669,933 A | 9/1997 | Simon et al. | 600/200 |
| 5,681,347 A | 10/1997 | Cathcart et al. | 606/200 |
| 5,690,671 A | 11/1997 | McGurk et al. | 606/200 |
| 5,693,067 A | 12/1997 | Purdy | 606/200 |
| 5,695,525 A | 12/1997 | Mulhauser et al. | 623/11 |
| 5,702,421 A | 12/1997 | Schneidt | 606/213 |
| 5,709,224 A | 1/1998 | Behl et al. | 128/898 |
| 5,709,707 A | 1/1998 | Lock et al. | 606/213 |
| 5,725,552 A | 3/1998 | Kotula et al. | 606/213 |
| 5,725,568 A | 3/1998 | Hastings | 623/11.21 |
| 5,733,294 A | 3/1998 | Forber et al. | 606/151 |
| 5,735,290 A | 4/1998 | Sterman et al. | 128/898 |
| 5,749,883 A | 5/1998 | Halpern | 606/159 |
| 5,749,894 A | 5/1998 | Engelson | 606/213 |
| 5,766,219 A | 6/1998 | Horton | 606/191 |
| 5,769,816 A | 6/1998 | Barbut et al. | 604/96 |
| 5,776,097 A | 7/1998 | Massoud | 604/500 |
| 5,782,860 A | 7/1998 | Epstein et al. | 606/213 |
| 5,810,874 A | 9/1998 | Lefebvre | 606/200 |
| 5,823,198 A | 10/1998 | Jones et al. | 128/899 |
| 5,830,228 A | 11/1998 | Knapp et al. | 606/195 |
| 5,836,913 A | 11/1998 | Orth et al. | 604/107 |
| 5,836,968 A | 11/1998 | Simon et al. | 606/200 |
| 5,846,260 A | 12/1998 | Maahs | 606/200 |
| 5,846,261 A | 12/1998 | Kotula et al. | 606/213 |
| 5,849,005 A | 12/1998 | Garrison et al. | 606/1 |
| 5,851,232 A | 12/1998 | Lois | 623/1 |
| 5,855,597 A | 1/1999 | Jayaraman | 623/1 |
| 5,865,791 A | 2/1999 | Whayne et al. | 604/49 |
| 5,865,802 A | 2/1999 | Yoon et al. | 604/104 |
| 5,868,708 A | 2/1999 | Hart et al. | 604/104 |
| 5,876,367 A | 3/1999 | Kaganov et al. | 604/8 |
| 5,882,340 A | 3/1999 | Yoon | 604/164.12 |
| 5,885,258 A | 3/1999 | Sachdeva et al. | 604/530 |
| 5,895,399 A | 4/1999 | Barbut et al. | 606/159 |
| 5,904,703 A | 5/1999 | Gilson | 606/213 |
| 5,906,207 A | 5/1999 | Shen | 128/898 |
| 5,910,154 A | 6/1999 | Tsugita et al. | 606/200 |
| 5,911,734 A | 6/1999 | Tsugita et al. | 606/200 |
| 5,916,236 A | 6/1999 | Muijs Van de Moer et al. | 606/213 |
| 5,928,192 A | 7/1999 | Maahs | 604/96 |
| 5,928,260 A | 7/1999 | Chin et al. | 606/200 |
| 5,935,147 A | 8/1999 | Kensey et al. | 606/213 |
| 5,935,148 A | 8/1999 | Villar et al. | 606/213 |
| 5,941,249 A | 8/1999 | Maynard | 128/898 |
| 5,947,997 A | 9/1999 | Pavcnik et al. | 606/213 |
| 5,951,589 A | 9/1999 | Epstein et al. | 606/213 |
| 5,954,694 A | 9/1999 | Sunseri | 604/96 |
| 5,957,940 A | 9/1999 | Tanner et al. | 606/155 |
| 5,976,174 A | 11/1999 | Ruiz | 606/213 |
| 5,980,555 A | 11/1999 | Barbut et al. | 606/200 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,007,523 A | 12/1999 | Mangosong | 604/284 |
| 6,007,557 A | 12/1999 | Ambrisco et al. | 606/200 |
| 6,010,517 A | 1/2000 | Baccaro | 606/151 |
| 6,010,522 A | 1/2000 | Barbut et al. | 606/200 |
| 6,024,754 A | 2/2000 | Engelson | 606/213 |
| 6,024,755 A | 2/2000 | Addis | 606/213 |
| 6,024,756 A | 2/2000 | Huebsch et al. | 606/213 |
| 6,027,520 A | 2/2000 | Tsugita et al. | 606/200 |
| 6,033,420 A | 3/2000 | Hahnen | 606/185 |
| 6,036,720 A | 3/2000 | Abrams et al. | 606/213 |
| 6,042,598 A | 3/2000 | Tsugita et al. | 606/200 |
| 6,048,331 A | 4/2000 | Tsugita et al. | 604/96 |
| 6,051,014 A | 4/2000 | Jang | 606/200 |
| 6,051,015 A | 4/2000 | Maahs | 606/200 |
| 6,056,720 A | 5/2000 | Morse | 604/96 |
| 6,063,070 A | 5/2000 | Eder | 606/1 |
| 6,068,621 A | 5/2000 | Balceta et al. | 604/500 |
| 6,074,357 A | 6/2000 | Kaganov et al. | 604/8 |
| 6,079,414 A | 6/2000 | Roth | 128/898 |
| 6,080,182 A | 6/2000 | Shaw et al. | 606/213 |
| 6,080,183 A | 6/2000 | Tsugita et al. | 606/213 |
| 6,083,239 A | 7/2000 | Addis | 606/200 |
| 6,132,438 A | 10/2000 | Fleischman et al. | 606/139 |
| 6,136,016 A | 10/2000 | Barbut et al. | 606/200 |
| 6,139,527 A | 10/2000 | Laufer et al. | 604/114 |
| 6,152,144 A | 11/2000 | Lesh et al. | 128/898 |

FOREIGN PATENT DOCUMENTS

| | | | |
|---|---|---|---|
| WO | WO 98/23322 | 6/1998 | |
| WO | WO 99/05977 | 2/1999 | A61B/17/12 |
| WO | WO 99/07289 | 2/1999 | A61B/17/00 |
| WO | WO 99/08607 | 2/1999 | A61B/17/12 |
| WO | WO 99/30640 | 6/1999 | A61F/2/06 |
| WO | WO 00/27292 | 5/2000 | A61B/17/08 |
| WO | WO 01/21247 | 3/2001 | A61M/29/00 |

OTHER PUBLICATIONS

Cragg et al., "Nonsurgical Placement of Arterial Endoprostheses: A New Technique Using Nitinol Wire," *Radiology* vol. 147, No. 1, pp. 261–263, Apr. 1983.

Cragg. et al., "A New Percutaneous Vena Cava Filter", *ALJ*, 141: 601–604, Sep. 1983.

Sugita et al., "Nonsurgical Implantation of a Vascular Ring Prosthesis Using Thermal Shape Memory Ti/Ni Alloy (Nitinol Wire)," *Trans. Am. Soc. Artif. Intern. Organs,* vol. XXXII, 30–34, 1986.

Ruttenberg, Nonsurgical Therapy of Cardiac Disorders, *Pediatric Consult,* vol. 5, No. 2, pages not numbered, 1986.

Rashkind et al., "Nonsurgical Closure of patent ductus arteriosus: clinical application of the Rashkind PDA Occluder System," *Circulation* 75, No. 3, 583–592, 1987.

Lock et al., "Transcatheter Umbrella Closure of Congenital Heart Defects," *Circulation,* vol. 75, No. 3, 593–599, 1987.

Wessel, et al. "Outpatient Closure of the patent ductus arteriosus," *Circulation,* vol. 77, No. 5, 1068–1071, 1988.

Lock et al., "Transcatheter Closure of Atrial Septal Defects," *Circulation,* vol. 79, No. 5, 1091–1099, May 1989.

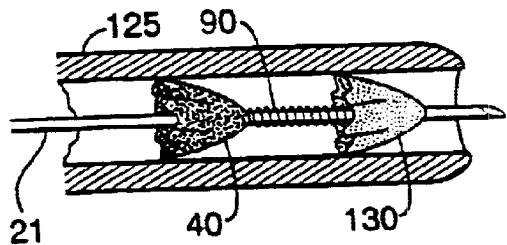
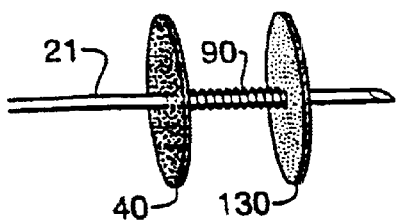
FIG. 5　　　　FIG. 6
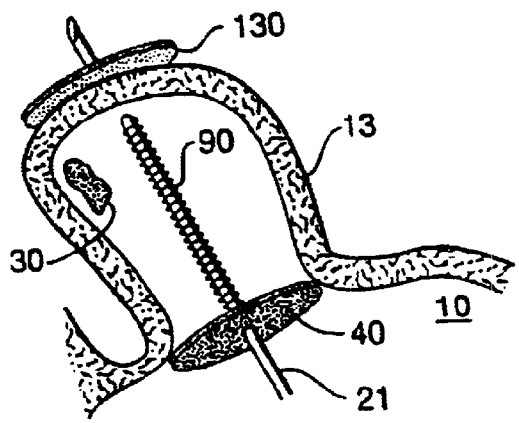
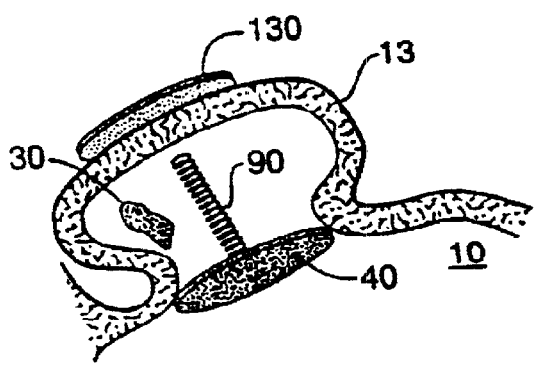
FIG. 7　　　　FIG. 8
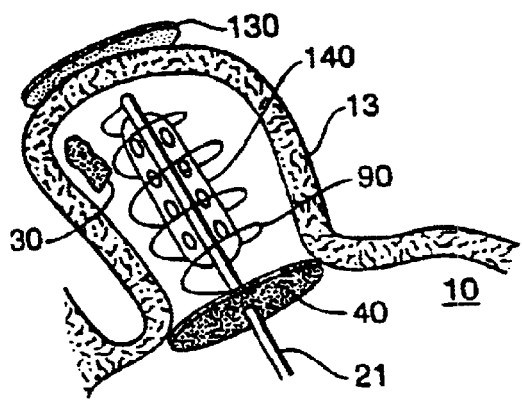
FIG. 9

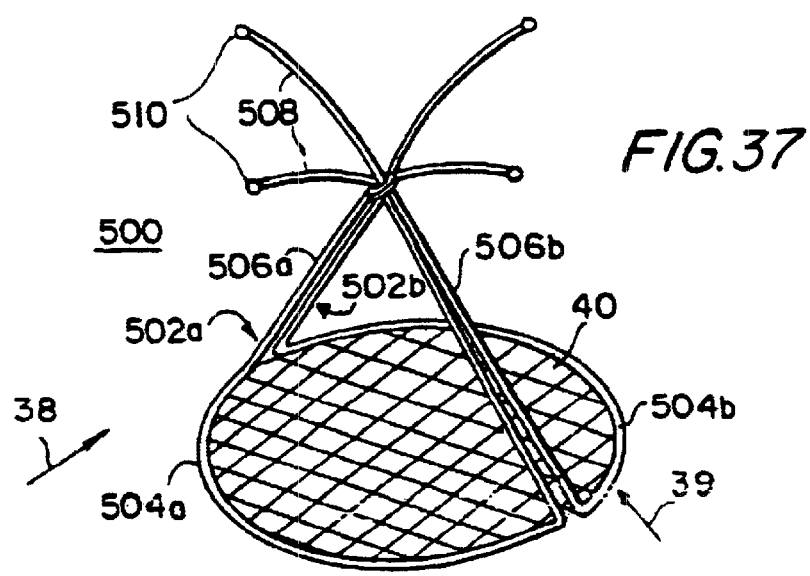
FIG. 37
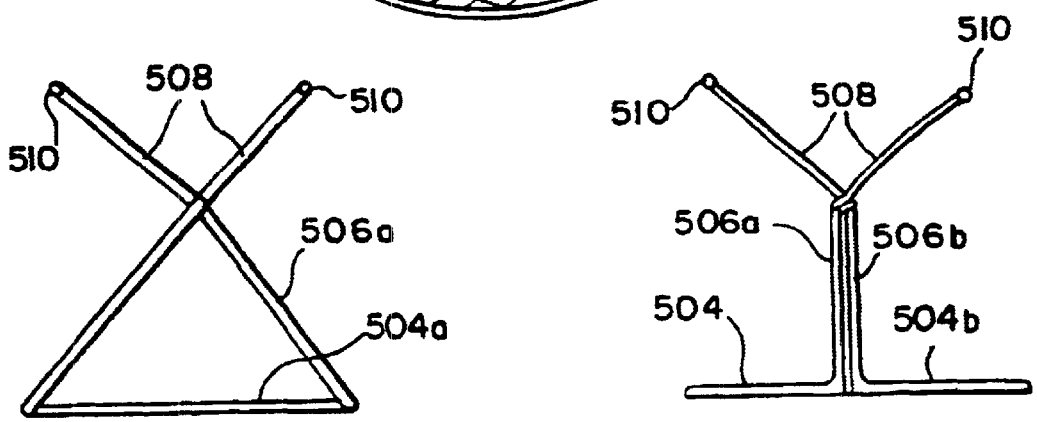
FIG. 38
FIG. 39
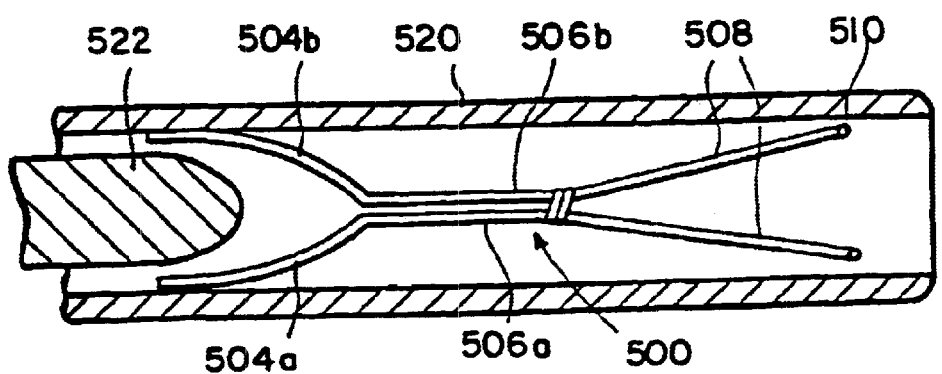
FIG. 40

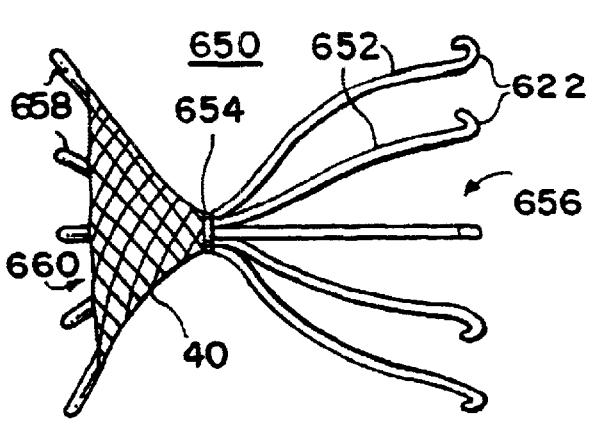
FIG.44
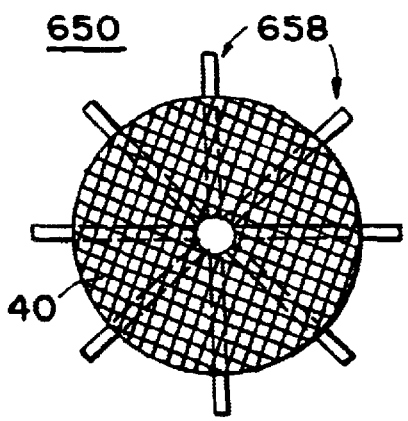
FIG.45
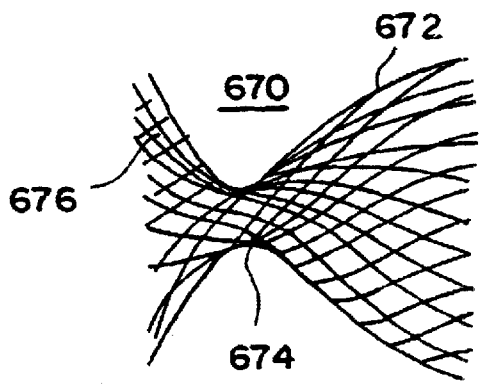
FIG.46
FIG.47
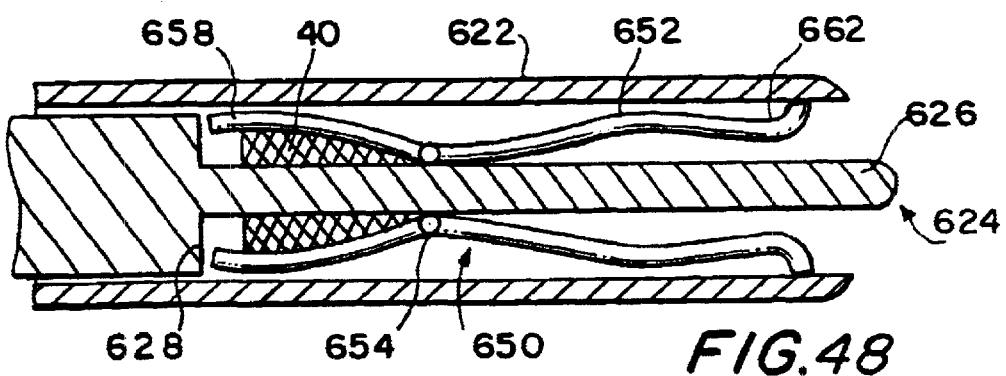
FIG.48

BARRIER DEVICE FOR COVERING THE OSTIUM OF LEFT ATRIAL APPENDAGE

This application is a continuation-in-part of application No. 09/614,091, filed Jul. 11, 2000, which is a continuation-in-part of application No. 09/428,008, filed Oct. 27, 1999, both of which are incorporated by reference in their entirety herein. This application also claims the benefit of U.S. provisional application No. 60/196,454, filed Apr. 11, 2000, U.S. provisional application No. 60/206,967, filed May 25, 2000, U.S. provisional application No. 60/209,511, filed Jun. 5, 2000, U.S. provisional application No. 60/211,896, filed Jun. 16, 2000, and U.S. provisional application No. 60/217,125, filed Jul. 10, 2000, all of which are incorporated by reference in their entirety herein.

BACKGROUND OF THE INVENTION

1. Field of the Invention

The invention relates to a membrane structure applied to or across the ostium of an atrial appendage to prevent a thrombus from leaving the atrial appendage.

2. Description of the Related Art

There are a number of heart diseases (e.g., coronary artery disease, mitral valve disease) that have various adverse effects on the heart. An adverse effect of certain cardiac diseases, such as mitral valve disease, is atrial (or auricular) fibrillation. Atrial fibrillation may result in pooling of blood in the left atrial appendage. Blood pooling may also be spontaneous. When blood pools in the atrial appendage, blood clots can form and accumulate therein, build upon themselves, and propagate out from the atrial appendage into the atrium. These blood clots can then enter the systemic or pulmonary circulations and cause serious problems if they migrate from the atrial appendage and become free in the blood stream and embolize distally into the arterial system. Similar problems also occur when a blood clot extending from an atrial appendage into an atrium breaks off and enters the blood supply. Since blood from the left atrium and ventricle supply the heart and brain, blood clots from the atrial appendages can obstruct blood flow therein causing heart attacks, strokes or other organ ischemia. It is therefore necessary to find a means of preventing blood clots from forming in the atrial appendages and to prevent these blood clots, once formed, from leaving the atrial appendages to the heart, lungs, brain or other circulations of the patient which can cause heart attacks or strokes or other organ ischemia.

U.S. Pat. No. 5,865,791 relates to the reduction of regions of blood stasis and ultimately thrombus formation in such regions, particularly in the atrial appendages of patients with atrial fibrillation. More specifically, the '791 patent relates to procedures and devices for affixing the atrial appendages in an orientation that prevents subsequent formation of thrombus. In the '791 patent, the appendage is removed from the atrium by pulling on it and by putting a loop around it to form a sack of the atrial appendage and then cutting it off from the rest of the heart.

U.S. Pat. No. 5,306,234 relates to a method for surgically closing the passage between the atrium and the atrial appendage or severing the atrial appendage.

Other methods of treatment include surgically removing the atrial appendages to prevent blood stasis in the atrial appendages.

SUMMARY OF THE INVENTION

The invention provides a membrane that substantially prevents blood clots formed in the atrial appendages from exiting therefrom. Such clots may cause heart attacks, strokes and other embolic events if allowed to leave the atrial appendage and enter the bloodstream. The membrane is permanently positioned across the ostium of the atrial appendage by direct securement means to the ostium or the atrial wall adjacent the ostium.

The membrane effectively isolates blood clots inside the left atrial appendage from leaving and entering the atrium. It may be larger than the ostium of the appendage, and extend over an area larger than the ostium. The membrane may be percutaneously delivered to the ostium of the atrial appendage by a catheter and then may be expanded for positioning across or over the ostium.

According to one embodiment, the membrane is impermeable to blood flow. This membrane inhibits thrombus in the left atrial appendage from exiting and entering the bloodstream. The membrane also prevents blood from flowing into or out of the left atrial appendage.

According to another embodiment, the membrane itself is permeable to permit blood flow across the membrane. By allowing the such blood flow across the membrane, the permeable structure minimizes any pressure gradient between the atrial appendage and the atrium in a controlled manner. Moreover, the permeable membrane acts as a filter in allowing blood to flow across, but substantially inhibits the passage of thrombus therethrough.

The permeable filtering membrane may eventually become infiltrated with cells. The permeable filtering membrane allows such tissue growth which may begin along the outer periphery of the structure. Such tissue growth minimizes uncontrolled leakage about the periphery of the filtering membrane and may assist in attachment of the filtering membrane across the ostium to tissue surrounding the ostium. The filtering membrane may be coated or covered with an anticoagulant or other compounds, such as, for example, heparin, or it may be treated to prevent thrombus from forming on the filtering membrane surface, to extend its patency or until it is infiltrated with cells and/or develops an endothelial covering.

There are many means for securing the membrane in position across the ostium of the atrial appendage. Direct securement means for the membrane may be provided by a biocompatible adhesive applied between the membrane and the ostium or the atrial wall. In this manner, the membrane can be adhered directly to the tissue. In another embodiment, direct securement is made by the use of staples, clips, sutures, wires, barbs, prongs or other methods of fixation which pass through the tissue of the ostium or atrial wall. In yet another embodiment, direct securement is achieved by the use of structure connected to the membrane which extends through the ostium and into the interior of the atrial appendage and engages the interior of the atrial appendage, wherein the interior wall of the atrial appendage may also include any portion of the ostium extending within the atrial appendage. The direct securement means may provide a self-centering feature for the membrane about the appendage ostium.

OBJECTS OF THE INVENTION

It is an object of the invention to provide a membrane between the atrium and atrial appendage to prevent blood clots from flowing therebetween.

It is an object of the invention to provide a membrane which is permanently implanted between the atrium and the atrial appendage by direct securement to the ostium or the atrial wall adjacent the ostium.

It is an object of the invention to provide a membrane between the atrium and the atrial appendage which is impermeable to blood flow or the passage of thrombus.

It is an object of the invention to provide a filtering membrane between the atrium and atrial appendage to allow blood flow across the filter, e.g., to reduce any hemodynamic pressure differential therebetween.

It is an object of the invention to prevent blood clots from forming in the atrial appendage.

It is an object of the invention to position across the ostium of the atrial appendage a non-thrombogenic, biocompatible surface that prevents blood clots from forming.

It is an object of the invention to provide a permeable filtering membrane surface which may eventually become lined with endothelial or endocardial cells.

It is an object of the invention to isolate the atrial appendage from the atrium proper with respect to the passage of thrombus with a filtering membrane, while allowing communication through which blood may flow.

It is an object of the invention to minimally invasively prevent blood clots from forming in the atrial appendages and escaping therefrom.

It is an object of the invention to prevent thrombus by use of heparin, other antithrombogenic substances, or other compounds on or eluted from the membrane.

It is an object of the invention to ensure the membrane is centered across or over the ostium of the atrial appendage.

It is an object of the invention to accurately place the membrane across or over the ostium of the atrial appendage.

Other objects, advantages and novel features of the present invention will become apparent from the following detailed description of the invention when considered in conjunction with the accompanying drawings.

BRIEF DESCRIPTION OF THE DRAWINGS

FIG. 5 is a partial cross sectional view of a delivery catheter having a disk, a spring and membrane therein in accordance with the invention.

FIG. 6 is a schematic view of a disk, spring and membrane after being expanded out of the delivery catheter of FIG. 5 in accordance with the invention.

FIG. 7 is a partial cross sectional view of a portion of a heart showing an atrium and its associated atrial appendage having a disk, a membrane and a spring therebetween in accordance with the invention.

FIG. 8 is a partial cross sectional view of a portion of a heart showing an atrium and its associated atrial appendage shown in a collapsed position in accordance with the invention.

FIG. 9 is a partial cross sectional view of a portion of a heart showing an atrium and its associated atrial appendage having a disk, a spring, a membrane and vacuum in the catheter in accordance with the invention.

FIG. 37 illustrates yet another embodiment of the filtering membrane and apparatus for attaching the filtering membrane in accordance with the invention.

FIG. 38 is an elevational view taken from direction 38 of FIG. 37 in accordance with the invention.

FIG. 39 is elevational view taken from direction 39 of FIG. 37 in accordance with the invention.

FIG. 40 is a sectional view illustrating the apparatus of FIGS. 37–39 along with additional apparatus in accordance with the invention.

FIG. 44 illustrates a further embodiment of the apparatus in accordance with the invention.

FIG. 45 is an end view of the apparatus of FIG. 44 in accordance with the invention.

FIG. 46 illustrates a still further embodiment of the apparatus in accordance with the invention.

FIG. 47 illustrates additional apparatus for use with the apparatus of FIGS. 44–46 in accordance with the invention.

FIG. 48 is an enlarged sectional view of the apparatus of FIG. 47 in accordance with the invention.

DESCRIPTION OF THE PREFERRED EMBODIMENTS

Although atrial fibrillation may result in the pooling of blood in the left atrial appendage and the majority of use of the invention is anticipated to be for the left atrial appendage, the invention may also be used on the right atrial appendage and in general for placement across any aperture in the body in which blood clots are substantially prevented from escaping from the cavity and entering into the bloodstream.

Figure 4:
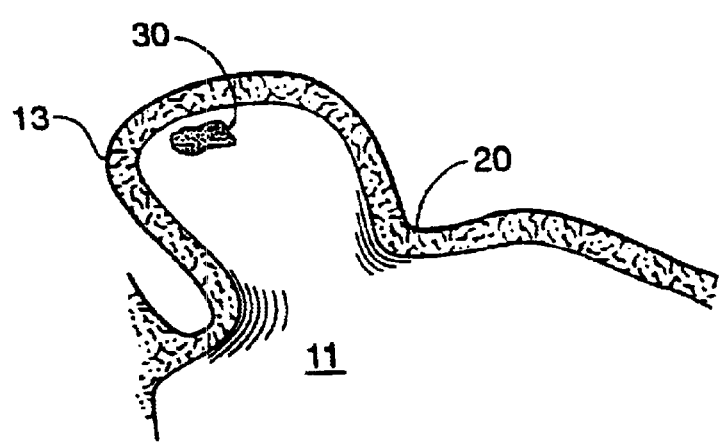
FIG. 4 is a partial cross sectional view of a portion of a heart showing an atrium and its associated atrial appendage.

As shown in FIG. 4, a thrombus, blood clot, or emboli 30 (collectively referred to as a thrombus) may occur from pooling of blood in the left atrial appendage 13 due to poor circulation of blood therein when the patient experiences atrial fibrillation. When blood pools in the left atrial appendage 13, thrombus 30 can accumulate therein, build upon itself, and propagate out from the left atrial appendage 13 into the left atrium 11, thus leaving the heart and entering the blood stream. Once in the bloodstream, such thrombus can block blood flow to the heart, brain, other organs, or peripheral vessels if it becomes lodged in the arteries thereof. Heart attack, a stroke, or ischemia may result.

To prevent thrombus 30 from forming in the left atrial appendage 13, or to prevent thrombus formed therein from leaving and entering the blood stream which may cause a heart attack, a stroke or ischemia, a membrane 40 is permanently attached over or across the ostium 20 of the atrial appendage 13. The membrane 40 can be made of biocompatible materials, such as, for example, ePFTE (e.g., Gortex®), polyester (e.g., Dacron®), PTFE (e.g., Teflon®), silicone, urethane, metal fibers, or other biocompatible polymers.

For each of the embodiments described hereinbelow, the membrane 40 may be substantially impermeable with respect to the flow of blood. For an impermeable membrane, neither blood nor thrombus is permitted to flow through the membrane. As described hereinabove, this structure prevents thrombus inside the atrial appendage from entering the bloodstream and causing heart attack, stroke, or ischemia. The impermeable membrane may be fabricated from materials described above, such as polyurethane, polyester (e.g., Dacron®), ePFTE (e.g., Gortex®) in textile, braid, or substrate form. The impermeable membrane could also be comprised of a combination of two or more materials. In some cases, the outer periphery of the membrane may be supported by struts fabricated from metal (e.g., stainless steel or nitinol) or plastic, or by cells or braid. (See, e.g., FIGS. 20, 22, 24, 50, 56). This additional structure may provide additional securement of the outer periphery of the membrane against the atrial wall surrounding the ostium in order to provide a leakproof seal.

According to another embodiment, each of the membrane structures 40 described herein may alternatively be substantially permeable with respect to the flow of blood therethrough. The permeable membrane may also act as a filtering membrane in that it will substantially inhibit thrombus from passing therethrough. The permeable filtering membrane may have pore sizes ranging from about 50 to about 400 microns. It is also contemplated that the pores may also be larger or smaller as indicated by the circumstances, provided such pores substantially inhibit thrombus from passing therethrough. The open area of the filtering membrane is preferably at least 20% of the overall surface area, although a range of about 25–60% may be preferred. The structure of the filtering membrane is preferably a two-dimensional screen, a cellular matrix, a woven or non-woven mesh, or the like. The filtering membrane may also be a permeable metal or a metal mesh of fine fibers. The filtering membrane may be coated or covered with an anticoagulant, such as heparin, or another compound, or treated to provide antithromogenic properties.

The permeability of the filtering membrane, described above, allows blood to flow therethrough while blocking or inhibiting the passage of thrombus, clots, or emboli formed within the atrial appendage from entering the atrium of the heart and, eventually, the patient's bloodstream.

The characteristic of allowing the flow of blood through the filtering membrane provides several advantages. For example, the left atrial appendage inherently contracts during normal cardiac function to force blood through the heart. These contractions result in blood flow through the ostium of the left atrial appendage. Allowing blood flow through the filtering membrane substantially reduces any pressure gradient that may exist between the appendage and the atrium.

The reduction of the pressure gradient may be helpful to the patient during recovery from the implantation of the filtering membrane structure in the atrial appendage. More particularly, the heart is able to more gradually adapt to the presence of the filtering membrane when blood is permitted to flow through the membrane, and consequently through the ostium of the left atrial appendage.

The filtering function may also reduce the risk of leakage about the periphery of the filtering membrane, or of dislodgement of the filtering membrane that may result from the exertion of pressure against the surface of the filtering membrane. Allowing the blood flow across the filtering membrane may relieve this pressure, sufficiently and in a controlled manner, to reduce such leakage or dislodgement.

Tissue ingrowth may provide additional securement of the filtering membrane to the ostium. More particularly, the growth of tissue may occur along the outer periphery of the filtering membrane or supporting structure adjacent the ostium. This tissue growth, in cooperation with the pressure relief provided by the permeable structure, may provide additional means of reducing leakage about the periphery of the filtering membrane. Tissue growth may eventually cover additional surface area of the filtering membrane.

The membrane 40 placed across or over the ostium 20 should be antithrombotic. In order to make the membrane antithrombotic, heparin or other anticoagulants or antiplatelet agents may be used on the membrane 40.

When permeable filtering membranes 40 are used, an ingrowth of cells may eventually cover the membrane with endothelial cells. The endothelial cells present a smooth cellular wall covering the membrane which prevents thrombosis from occurring at the membrane.

Figure 1:
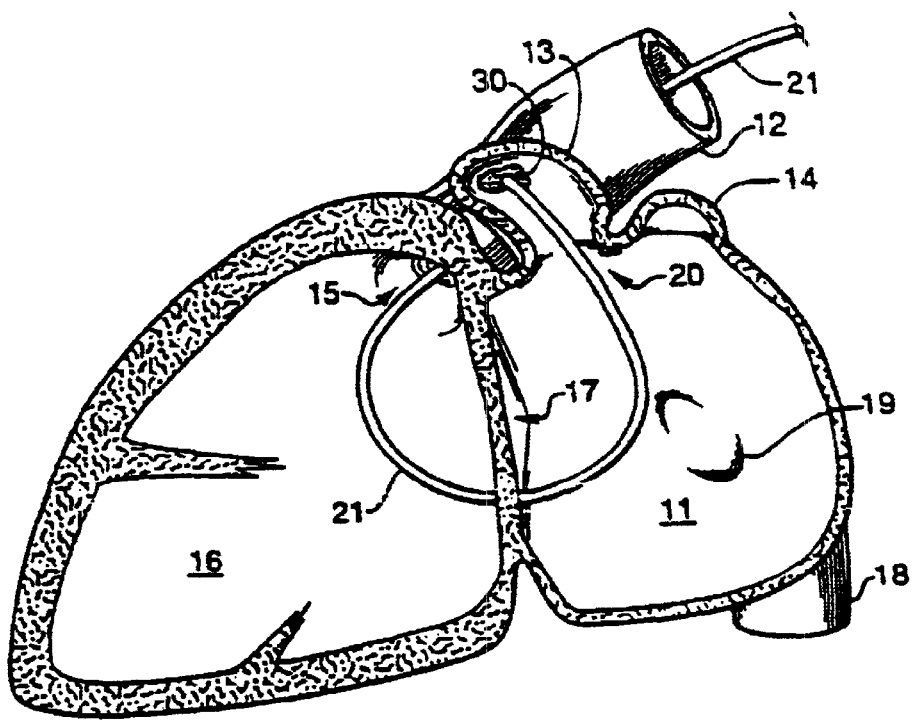
FIG. 1 is a partial cross sectional view of a heart showing a catheter entering the left atrial appendage using a retrograde procedure from the aorta in accordance with the invention.
Figure 2:
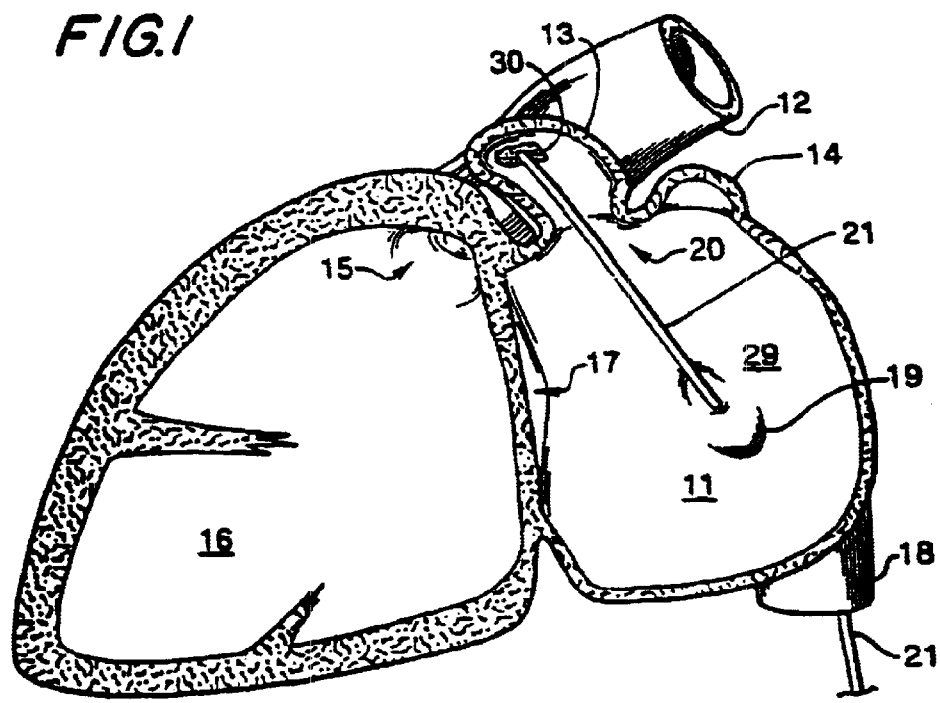
FIG. 2 is a partial cross sectional view of a heart showing a catheter entering the left atrial appendage using a transeptal procedure from the femoral vein or superior vena cava in accordance with the invention.

FIGS. 1 and 2 show a cross section of a human heart showing a thrombus 30 in the left atrial appendage 13. The figures also show the atrial appendage ostium 20 which is to have a membrane 40 placed over it to prevent the thrombus 30 from escaping out of the atrial appendage 13 into the left atrium 11 and thus into the blood stream, which could cause a stroke, a heart attack or ischemia.

Figure 3:
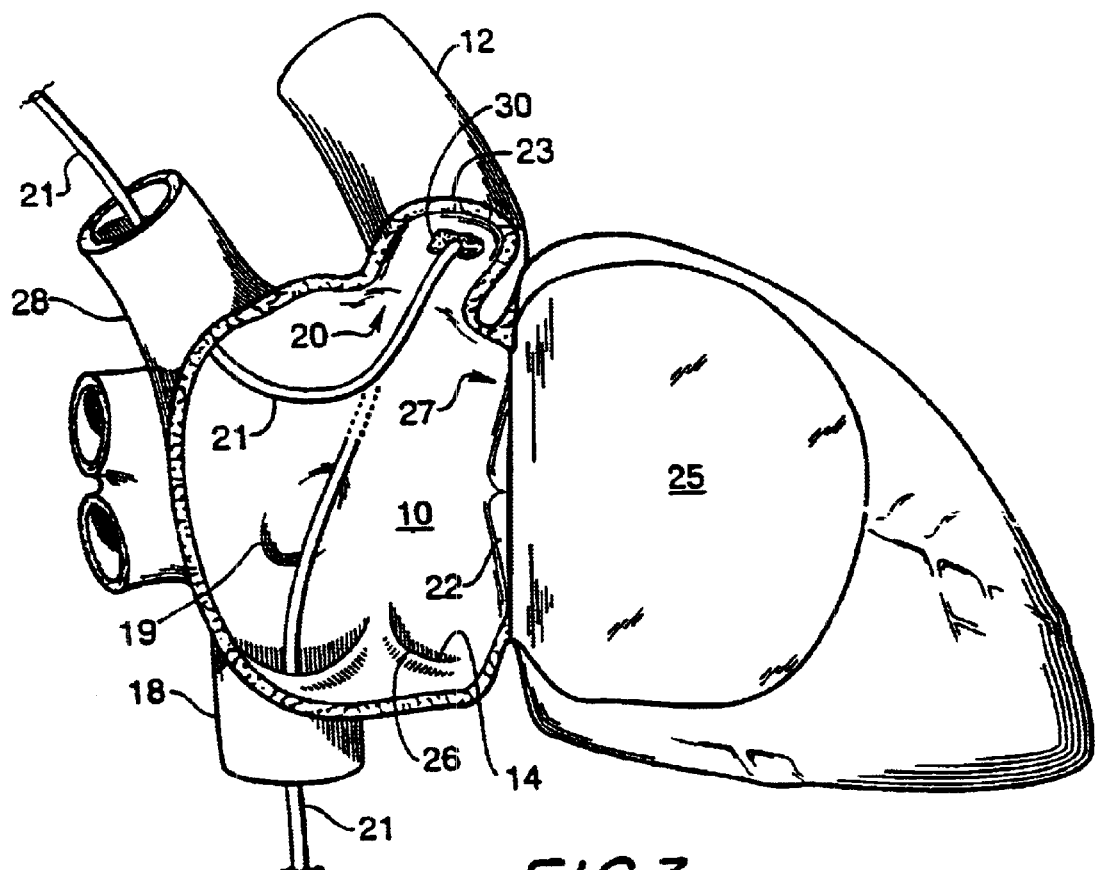
FIG. 3 is a partial cross sectional view of a heart showing a catheter entering the right atrial appendage from the jugular vein or optionally from the femoral vein in accordance with the invention.

FIG. 3 shows a cross section of a human heart showing a thrombus 30 in the right atrial appendage 23. The right atrial appendage 23 can be treated in the same manner as the left atrial appendage 13.

FIG. 4 shows a cross section of the left atrium 11, the ostium 20 and the left atrial appendage 13 having a thrombus 30 therein.

FIG. 5 shows a delivery catheter 125 containing a collapsed membrane 40 and a collapsed disk 130 connected to the membrane 40 by a spring 90 on catheter 21. The disk 130 may be made of a flexible woven metal or a flexible woven metal with a thin permeable polymer sandwiched inside. Disk 130 may also be a polymer weave. The disk 130 is flexible and compresses or folds so it fits into the delivery catheter 125 and expands to its desired shape after release from the delivery catheter 125. Similarly, membrane 40 compresses or folds to fit into the delivery catheter 125 and expands to its desired shape after release. Membrane 40 is larger than the ostium 20. FIG. 6 shows the membrane 40, disk 130 and spring 90 from FIG. 5 in an expanded configuration outside of the delivery catheter 125.

FIG. 6 shows the spring 90 connecting the membrane 40 and the disk 130 for urging them together. In other embodiments an elastic tether or a tether with teeth and a pawl on the membrane 40 to form a ratchet can also be used to pull the membrane 40 and the disk 130 together. Since membrane 40 is larger than the ostium 20, the outer periphery of membrane 40 is in contact with the atrial wall surrounding the ostium.

FIG. 7 shows the device of FIG. 5 applied to the left atrial appendage 13 having thrombus 30. After the device is applied, the spring 90 pulls the disk 130 toward the membrane 40, collapsing the left atrial appendage 13 and trapping the thrombus 30 therein as shown in FIG. 8. The spring 90 secures the outer periphery of the membrane 40 in direct engagement with the atrial wall surrounding the ostium 20.

FIG. 9 shows an alternate embodiment of the device in FIGS. 7 and 8 wherein the catheter 21 is equipped with a vacuum 140 for sucking out blood and thrombosis 30 found in the left atrial appendage 13. The vacuum 140 will help collapse the left atrial appendage 13 such that spring 90 need not be as large as in FIG. 7.

Figure 10:
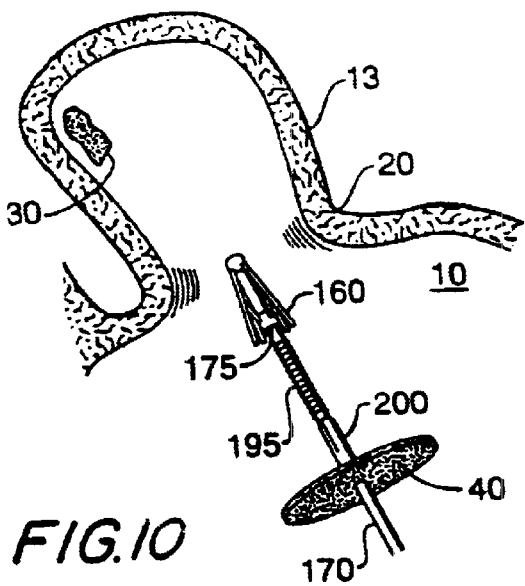
FIG. 10 is a partial cross sectional view of a portion of a heart showing an atrium and its associated atrial appendage showing an umbrella folded for entering the atrial appendage in accordance with the invention.
Figure 11:
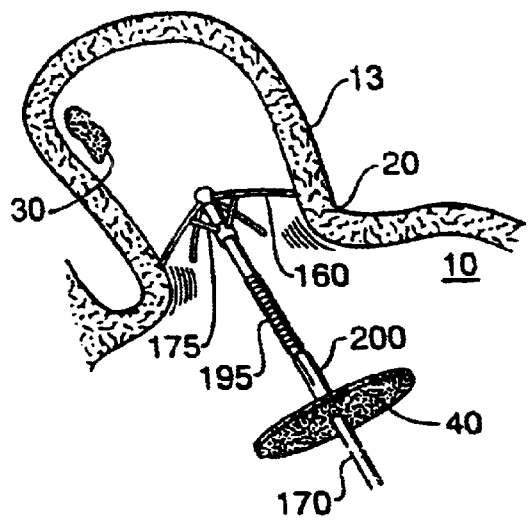
FIG. 11 is a partial cross sectional view of a portion of a heart showing an atrium and its associated atrial appendage showing the umbrella opened in the atrial appendage to secure the umbrella into the wall of the atrial appendage in accordance with the invention.
Figure 12:
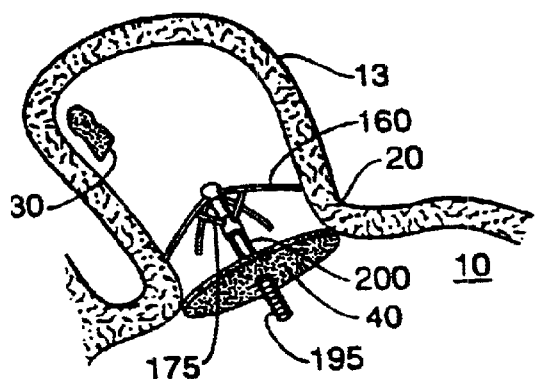
FIG. 12 is a partial cross sectional view of a portion of a heart showing an atrium and its associated atrial appendage showing the umbrella and membrane positioned across the ostium of the atrial appendage in accordance with the invention.

FIGS. 10–12 show another embodiment of the invention using an umbrella principle for securing the membrane 40 against the ostium 20. FIG. 10 shows closed umbrella struts 160 entering the ostium 20 of left atrial appendage 13. The membrane 40 is some distance back from the umbrella struts 160 at the bottom of the range of teeth 195 on pole 170. FIG. 11 shows the umbrella struts inside of the left atrial appendage 13 with the struts 160 open. Umbrella opening structure 175 on pole 170 pushes the struts out to the umbrella open position. The umbrella opening structure 175 can be pushed to the open position or have a spring loaded mechanism to push the struts 160 to the open position. The ends of the umbrella struts 160 engage the left atrial appendage wall around the ostium 20 and prevent the umbrella from being withdrawn from the left atrial appendage 13. The ends of the umbrella struts 160 that engage the atrial appendage wall may be blunted or have bulbs on the tips or have padding so as not to puncture the left atrial appendage 13. FIG. 12 shows the outer periphery of membrane 40 drawn up against the atrial wall surrounding the ostium 20 by ratcheting the membrane along pole 170. The pawl mechanism 200 engages teeth 195 on pole 170 and is moved forward to snugly position the membrane 40 across the ostium 20 such that the outer periphery of the membrane 40 is in direct engagement with the atrial wall surrounding the ostium.

Figure 13:
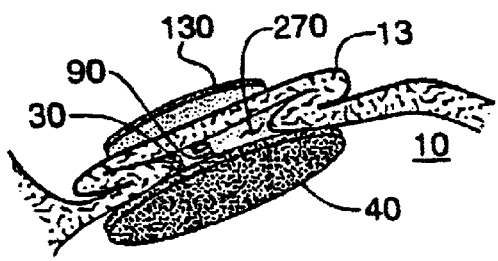
FIG. 13 is a partial cross sectional view of a portion of a heart showing an atrium and its associated atrial appendage showing the atrial appendage reduced to a minimum volume by a disk and spring squeezing the appendage against a membrane in accordance with the invention.

FIG. 13 shows the left atrial appendage 13 compressed such that the volume of the atrial appendage is reduced to almost nothing. With the volume reduced the atrial appendage will not have a large volume of blood which can produce a thrombus. In the embodiment shown disk 130 and spring 90 pull the left atrial appendage 13 toward membrane 40. Although FIG. 13 shows the use of a disk 130 and spring 90 to act on the left appendage, any method to reduce the volume of the atrial appendage as much as possible may be used.

As shown in FIG. 13 the membrane 40 is much larger than the ostium 20. The oversized membrane 40 may alternatively be used in all embodiments to ensure that the ostium 20 is completely covered. The spring 90 secures the outer periphery of the membrane 40 in direct engagement with the atrial wall surrounding the ostium 20. The membrane 40 has a structure which blocks or substantially inhibits thrombus, clots or emboli from entering the atrium, and eventually, the bloodstream of the patient.

Figure 14:
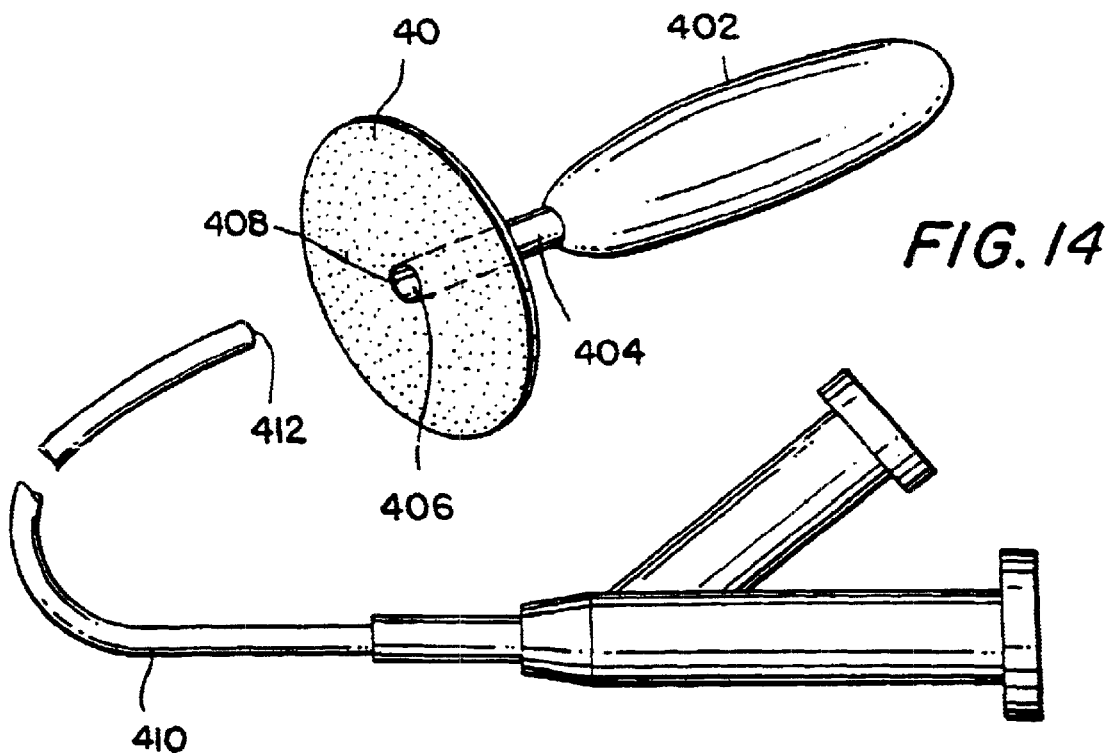
FIG. 14 is a perspective view of another embodiment of a filtering membrane and apparatus for installing the filtering membrane in accordance with the invention.
Figure 15:
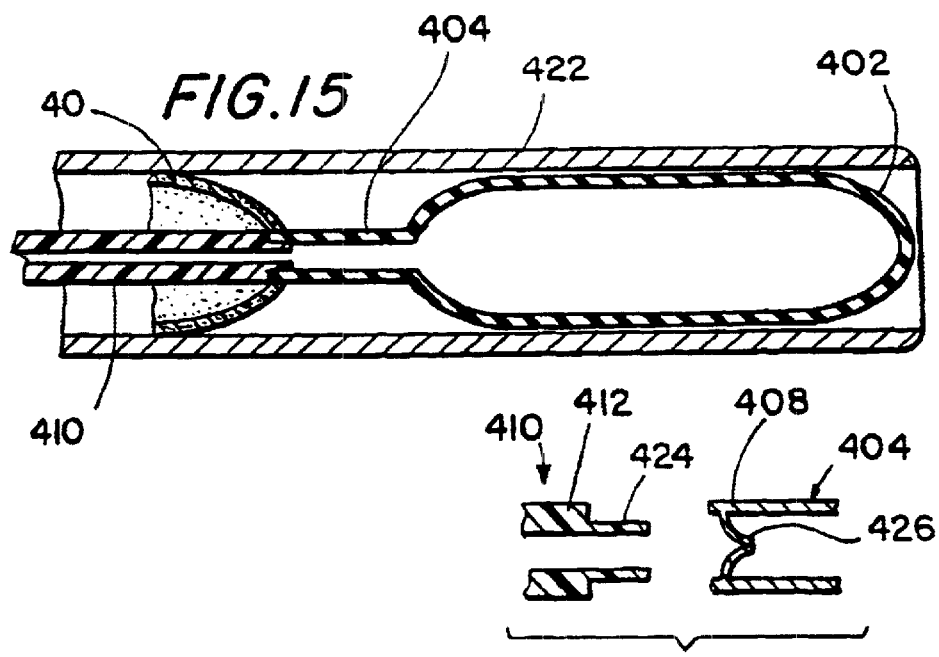
FIG. 15 is a sectional view of the filtering membrane and apparatus illustrated in FIG. 14, in accordance with the invention.

FIGS. 14–18 show another embodiment of the invention wherein the outer periphery of the membrane 40 is secured in direct engagement with the atrial wall surrounding the ostium 20 by an expandable structure, such as balloon structure 402. As illustrated in FIG. 15, balloon structure 402 may be manufactured from polymeric materials or similar materials known in the art. Tube 404 communicates with the internal cavity of balloon structure 402 for introducing saline or other appropriate fluid into the balloon structure 402. Membrane 40 is attached to tube 404 in any appropriate manner, such as adhesive, sutures, or other means, and is provided with an aperture 406 which permits access to an end portion of tube 404, which acts as a balloon introduction port 408 to allow the introduction of fluid into the balloon structure 402.

FIG. 14 also illustrates a structure for introducing fluid into the balloon structure 402, such as catheter apparatus 410. Catheter apparatus 410 includes an outlet port 412 at its distal end portion for ejecting fluid from the catheter apparatus 410. Outlet port 412 may be connected to the balloon introduction port 408, which in turn communicates with the internal lumen of tube 404 and the interior of balloon structure 402.

Figure 16:
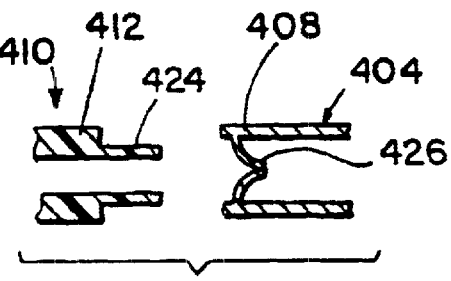
FIG. 16 is an enlarged view of a portion of the apparatus of FIG. 15 in accordance with the invention.

FIG. 15 illustrates the membrane 40, the balloon structure 402, the tube 404, together with the catheter 410 attached to the tube 404, in a compacted configuration within a delivery tube 422. More particularly, balloon structure 402 is in its collapsed state and membrane 40 is flexible and compressed or folded to fit into the delivery tube 422. Membrane 40 is designed to expand into a disc-like shape after release from tube 422. FIG. 16 illustrates the certain structures pertinent to the interconnection of catheter 410 with tube 404. More particularly, outlet port 412 of catheter 410 may be provided with narrow tube 424 which is received within balloon introduction port 408 and maintains a valve 426 in an open position when outlet port 412 is connected to inlet port 408. When outlet port 412 is removed from balloon introduction port 408, valve 426 may close to prevent fluid from leaving balloon structure 402, as shown in FIG. 16.

Delivery tube 422 may be introduced into the venous or arterial system at an appropriate location, and advanced to into the atrium of the heart with appropriate steering and visualization apparatus (not shown).

Figure 17:
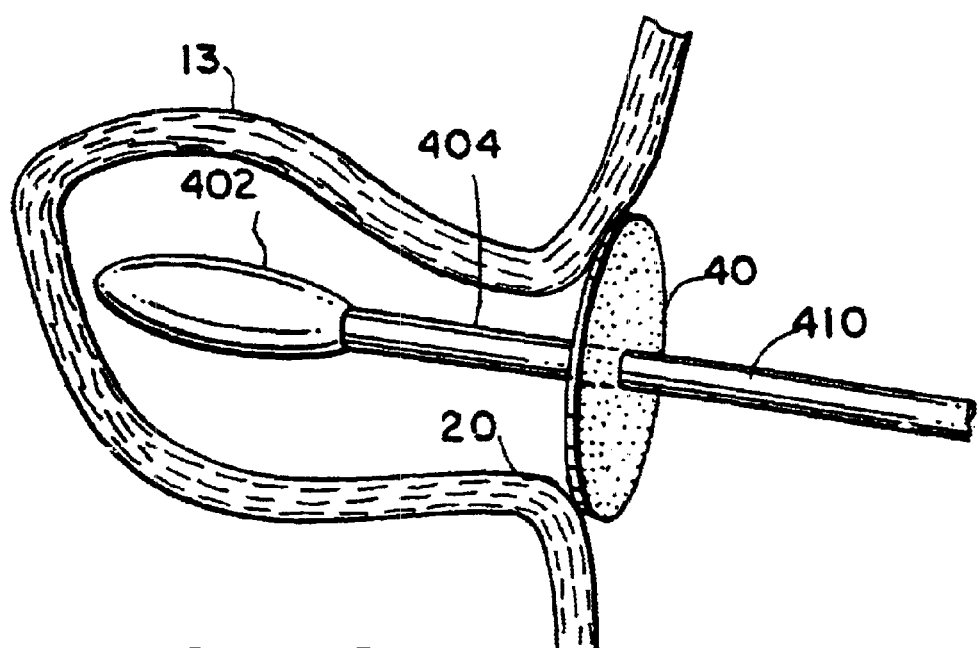
FIG. 17 is a partial cross-sectional view illustrating an early stage in the installation of the apparatus of FIG. 14, in accordance with the invention.
Figure 18:
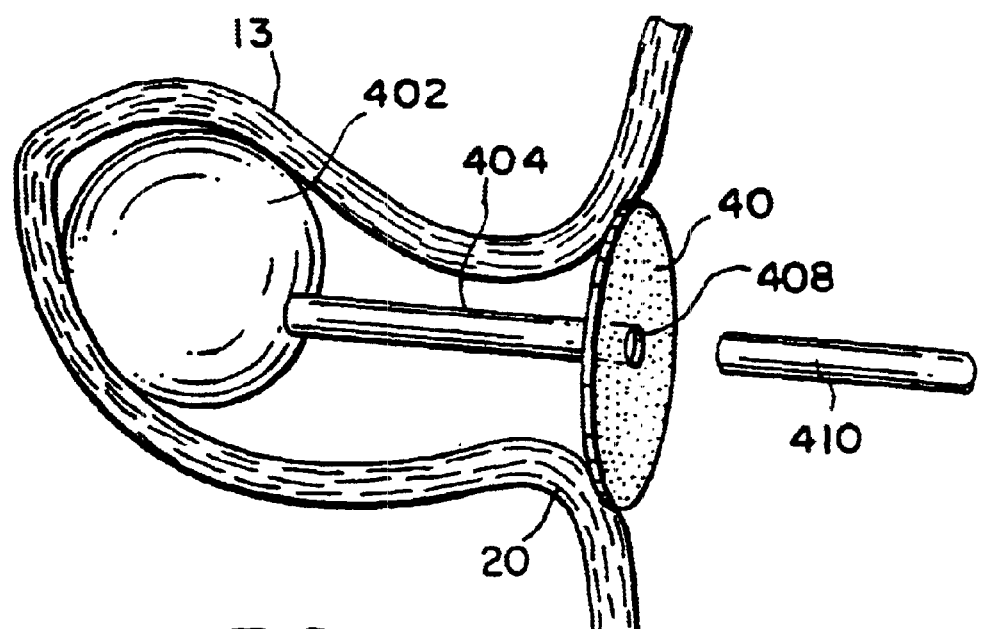
FIG. 18 is a partial cross-sectional view similar to FIG. 17, illustrating a later stage in the procedure in accordance with the invention.

FIG. 17 illustrates a later stage in the installation procedure wherein the membrane 40, the balloon structure 402, the tube 404, and the catheter 410 have been advanced from the delivery tube 422 (not shown in FIG. 17). The balloon structure 402 is positioned within the left atrial appendage 13 such that the outer periphery of membrane 40 is positioned adjacent the atrial wall surrounding the ostium 20. Fluid is subsequently introduced into the catheter 410 which passes through tube 404 to expand the balloon structure 402, as illustrated in FIG. 18. The balloon structure 402 expands within the atrial appendage 13 and secures the membrane 40 in position. The valve mechanism 426 (not shown in FIG. 18) of balloon introduction port 408 prevents the fluid from passing out of the balloon structure 402 when the catheter 410 is detached from the balloon port 408 and subsequently removed from the atrium. As described above, membrane 40 may have an impermeable structure which prevents thrombus for exiting the atrial appendage 13, but which also prevents blood flow through the membrane 40. Membrane 40 may alternatively be a permeable structure which allows blood to flow therethrough but which blocks or substantially inhibits thrombi, clots or emboli from exiting the atrial appendage 13, and entering the bloodstream of the patient.

Figure 19:
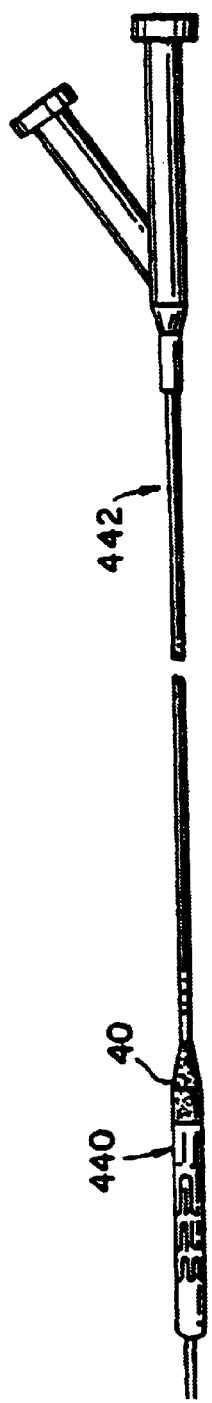
FIG. 19 illustrates another embodiment of the filtering membrane and apparatus for installing the filtering membrane in accordance with the invention.
Figure 20:
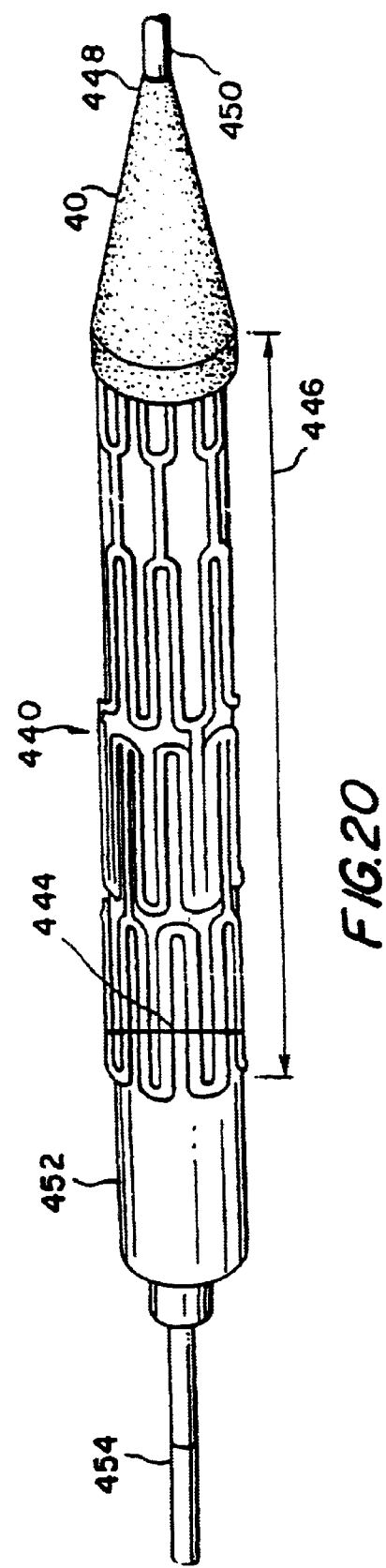
FIG. 20 is an enlarged view of the filtering membrane and apparatus illustrated in FIG. 19 in accordance with the invention.

FIGS. 19–31 illustrate yet another embodiment for attaching the membrane across the ostium 20 of the left atrial appendage 13. FIG. 19 illustrates the membrane 40, the attachment apparatus 440 for securing the membrane 40 across the ostium 20 of the atrial appendage 13, and catheter apparatus 442 for installing the attachment apparatus 440 and membrane 40. As FIG. 20 illustrates, attachment apparatus 440 and membrane 40 may be initially in a compacted configuration. Attachment apparatus 440 is preferably an expandable tubular apparatus having an initial diameter 444 of about 1–3 mm and an initial length 446 of about 0.5–6 cm. Attachment apparatus is preferably manufactured from a flexible material such as stainless steel, nitinol, nylon, polyester, PET, or polyethylene. Attachment apparatus 440 may be expanded by an expansion structure, such as balloon structure 452 or mechanical expansion structures 472 or 482. Alternatively, attachment apparatus 440 may be self-expanding, such that it is normally biased in an expanded position, such as that described with respect to FIG. 24, and deployed in a constrained position such as that described with respect to FIG. 20. Apparatus for constraining the self-expanding apparatus is typically a tube.

Membrane 40 is attached to attachment apparatus 440 at the proximal end thereof, in a loosely fitted, somewhat conical configuration and defines a central opening 448, which allows the catheter 450 of catheter apparatus 442 to pass through membrane 40, as will be described in greater detail herein. Alternatively, membrane 40 may also cover a greater portion of the length 446 of the attachment apparatus 440, or membrane 40 may cover the entire attachment apparatus 440 in a substantially sock-like fashion. Membrane 40 may be fabricated from a material that also has elastic characteristics which may expand from a first size to a second size.

Catheter 450 supplies expansion fluid, such as saline or contrast medium, into expandable structure, such as balloon structure 452, which is positioned within the interior lumen of attachment apparatus 440 in order to radially expand attachment apparatus 440 when it is positioned within the atrial appendage 13. Balloon structure 452 may include a distal, atraumatic tip portion 454, e.g., a flexible helical coil or soft plastic tip.

Figure 21:
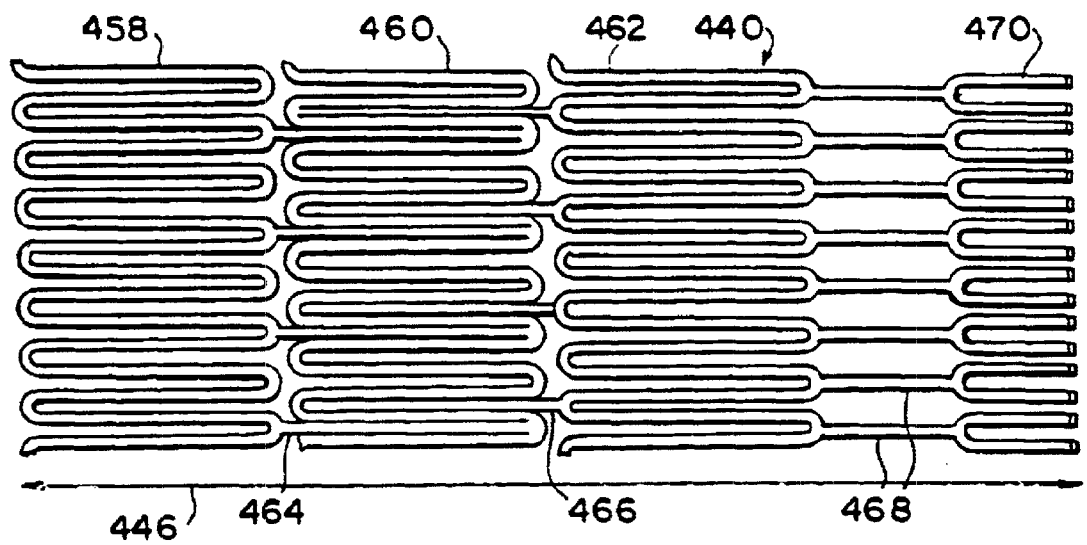
FIG. 21 is a planar development of the apparatus for attaching the filtering membrane illustrated in FIGS. 19–20 in accordance with the invention.
Figure 22:
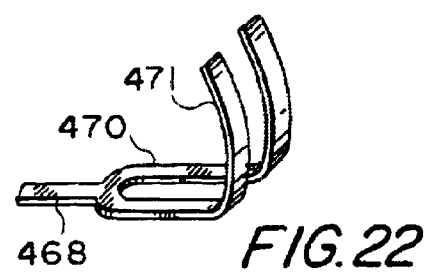
FIG. 22 is an enlarged perspective view of a portion of the apparatus of FIG. 21, in accordance with the invention.
Figure 23:
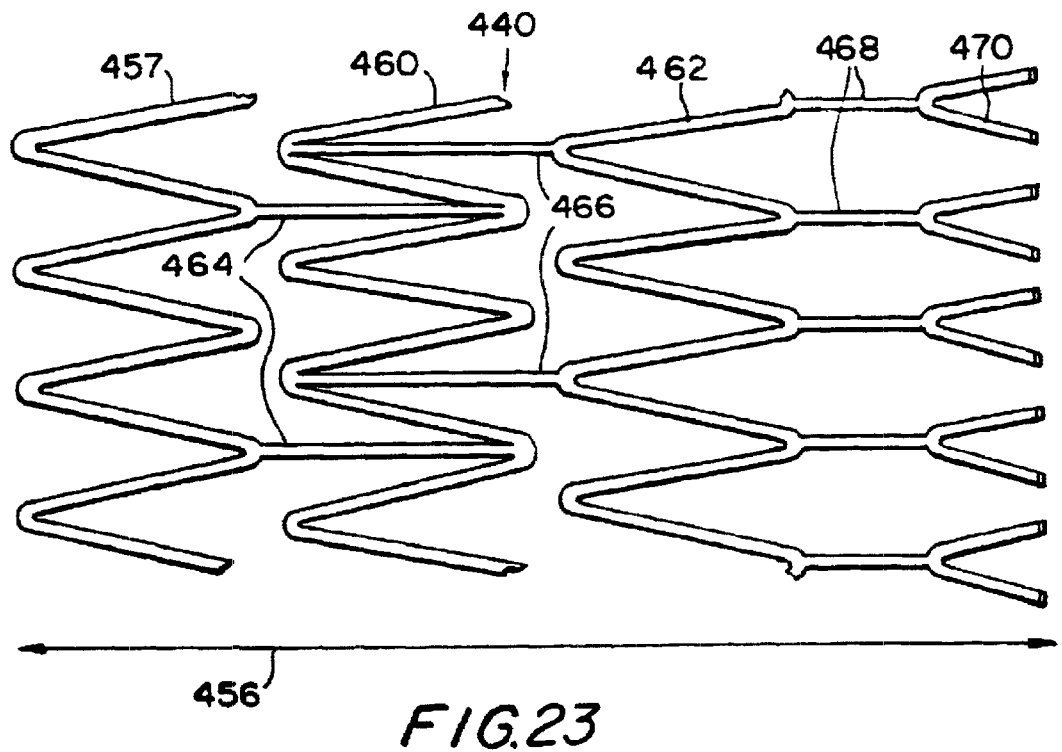
FIG. 23 is a planar development of the apparatus depicted in FIG. 21 in an expanded configuration, in accordance with the invention.

FIGS. 21 and 23 illustrate planar developments of attachment apparatus 440. The structure of attachment apparatus 440 preferably allows the length 446 of the apparatus in its initial configuration (FIG. 21) to remain substantially constant with respect to the length 456 in its expanded configuration (FIG. 23). In order to achieve this expansion while maintaining substantially constant length, attachment apparatus 440 is provided with a configuration having several serpentine segments 458, 460, and 462. Adjacent serpentine segments are interconnected by a plurality of longitudinal struts, e.g., rings 457 and 460 are interconnected by struts 464 and rings 460 and 462 are interconnected by struts 466. A plurality of members 470 at the distal end portion of apparatus 440 may provide an attachment point for the membrane 40. More particularly, radial members 471 are configured to extend radially outward (FIG. 22) to provide a location for attachment of the outer periphery of membrane 40 and to provide a surface for attachment to the atrial wall. As will be described herein, radial members 471 may be expanded to the radially outward configuration by an expansion member such as a balloon. In one embodiment, the materials or thickness of members 471 may be selected in order to allow members 471 to expand to a greater extent than the rest of the attachment member 440. Alternatively, members 471 may be fabricated from a self-expanding material, such as, e.g., nitinol, wherein members are normally biased in the radially outward configuration.

Figure 24:
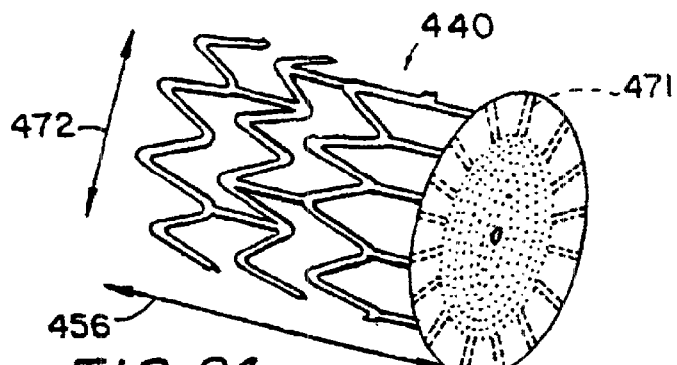
FIG. 24 is a perspective view of the filtering membrane and apparatus for attaching the filtering membrane of FIG. 20, illustrated in an expanded configuration in accordance with the invention.
Figure 30:
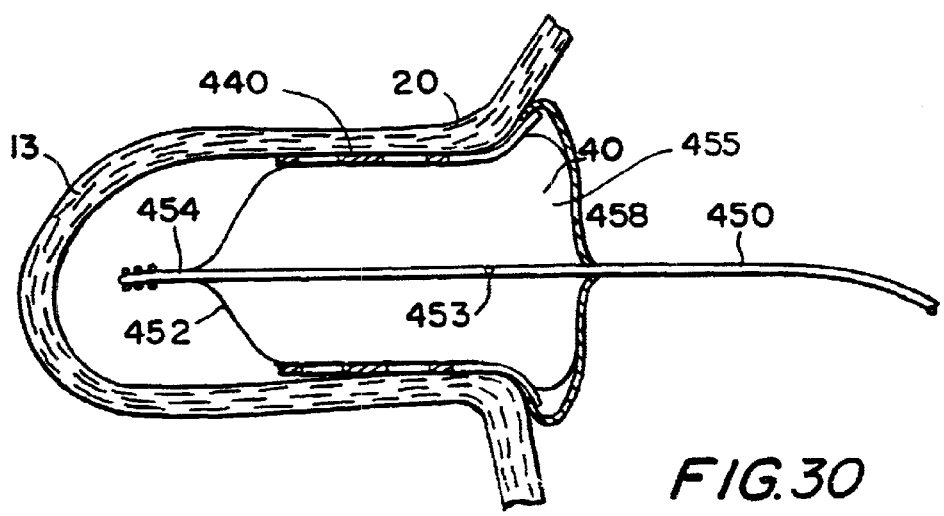
FIG. 30 is a partial cross-sectional view similar to FIG. 29 illustrating a later stage in the procedure in accordance with the invention.

FIG. 24 illustrates attachment member 440 in an expanded configuration, wherein length 456 remains substantially constant with respect to the length 446 of the configuration illustrated in FIG. 30. Diameter 472 is substantially larger than diameter 444 (FIG. 20) in order to secure itself against the interior of the atrial appendage 13 and to secure membrane 40 in direct engagement with the atrial wall surrounding the ostium 20, as will be described herein. Members 471 extend radially outward, and provide structure to the outer periphery of membrane 40.

FIGS. 25–28 illustrate several embodiments of the membrane 40. As described above, catheter 450 passes through opening 458 in membrane 40 in order to supply expansion fluid to expandable balloon structure 452. After balloon structure 452 has expanded the attachment apparatus 440 to the expanded configuration illustrated in FIG. 24, it may be necessary to remove balloon structure 452 by passing the balloon structure 452 proximally through membrane 40, and more particularly, through opening 458. The embodiments of membrane 40 illustrated in FIGS. 25–28 may facilitate the passage of balloon structure 452, or other interventional devices therethrough.

Figure 25:
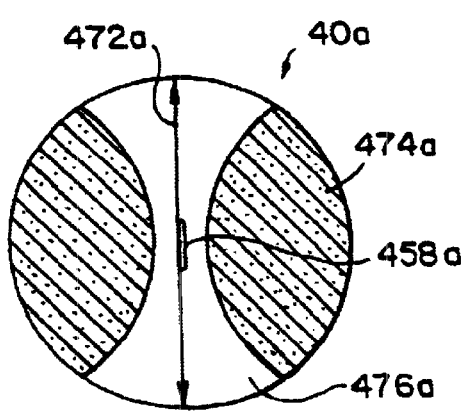
FIG. 25 is an elevational view of an embodiment of the filtering membrane in accordance with the invention.
Figure 26:
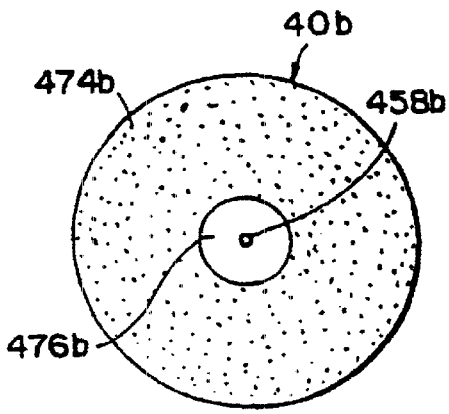
FIG. 26 is an elevational view of another embodiment of the filtering membrane in accordance with the invention.
Figure 27:
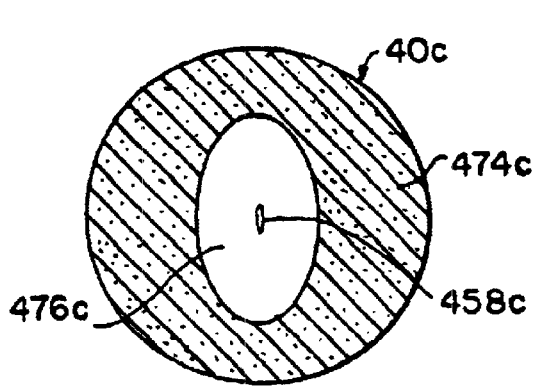
FIG. 27 is an elevational view of yet another embodiment of the filtering membrane in accordance with the invention.
Figure 28:
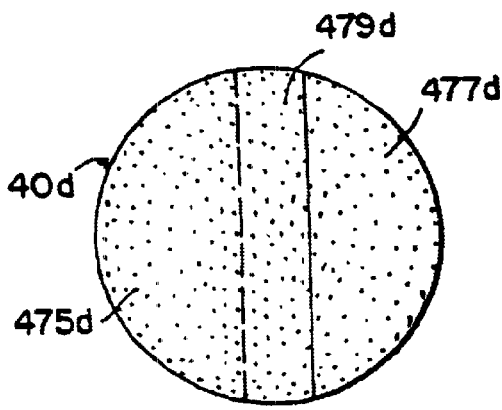
FIG. 28 is an elevational view of a further embodiment of the filtering membrane in accordance with the invention.

FIG. 25 illustrates membrane 40a having a composite construction comprising filtering section 474a and elastic section 476a. The filtering section 474a is fabricated from a filtering material that provides the function of filtering the blood to allow the blood to pass therethrough while blocking or substantially inhibiting the passage of clots, thrombus or emboli therethrough, as described above. The elastic section 476a is fabricated from an elastic material, e.g., silicone, urethane or other similar material, that stretches to enlarge opening 458a to allow the balloon structure 452 or other intervention devices, such as, e.g., wires, catheters or the like, to pass therethrough and to subsequently return to its initial size. The initial size of aperture 458a provides similar characteristic to inhibit clots, thrombus or emboli from passing through 458a as filtering material of filtering section 474a. In this configuration, elastic material 476a extends substantially across the entire diameter 472a of the membrane 40a.

Membrane 40b (FIG. 26) is constructed with a filtering section 474b (i.e., the same material as filtering section 474a) and an elastic section 476b (i.e., the same elastic material as elastic section 476a). In membrane 40b, the filtering section 474b substantially concentrically surrounds the elastic section 476b. The elastic section 476b is provided with an opening 458b that expands to allow the balloon structure 452 or other interventional devices to pass therethrough and to return to initial size in order to provide substantially the same characteristic of inhibiting the passage of thrombus, clots and emboli from passing therethrough as the filtering material of the filtering section 474b.

Membrane 40c (FIG. 27) is constructed with a filtering section 474c (i.e., the same material as filtering section 474a) and an elastic section 476c (i.e., the same elastic material as elastic section 476a). In membrane 40c, the filtering section 474c substantially concentrically surrounds an elastic section, such as substantially elliptical section 476c. The elastic section 476c is provided with an aperture, such as a slit 458c that expands to allow the balloon structure 452 or other interventional devices to pass therethrough and to return to initial size to provide substantially the same characteristic of inhibiting the passage of thrombus, clots and emboli from passing therethrough as the filtering material of the faltering section 474b.

Membrane 40d (FIG. 28) may be fabricated from the same material as filtering section 474a, above, in several sections, such as sections 475d and 477d, which overlap at region 479d to form an opening therethrough for balloon structure 452 or other interventional devices. It is further contemplated that three or more sections of filtering material may be used in an overlapping configuration, in a manner similar to, for example, the "aperture" configuration of an optical device. The balloon structure 452 may be passed through the opening between sections 475d and 477d. After the balloon structure 452 is removed, the overlapping structure substantially closes the opening and provides substantially the same characteristic of inhibiting the passage of thrombus, clots and emboli from passing therethrough as the filtering material of the filtering sections 475d and 477d.

Figure 29:
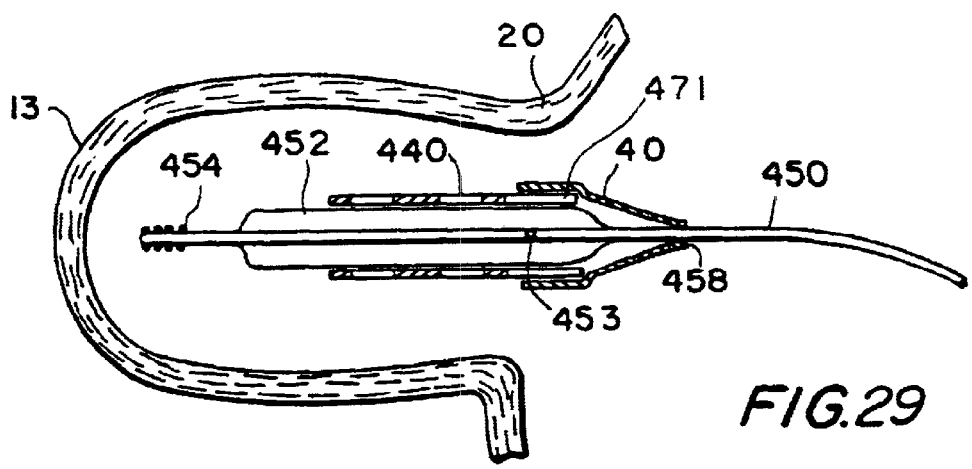
FIG. 29 is a partial cross-sectional view illustrating an early stage in the procedure of installing of the filtering membrane of FIGS. 19–28 in accordance with the invention.
Figure 31:
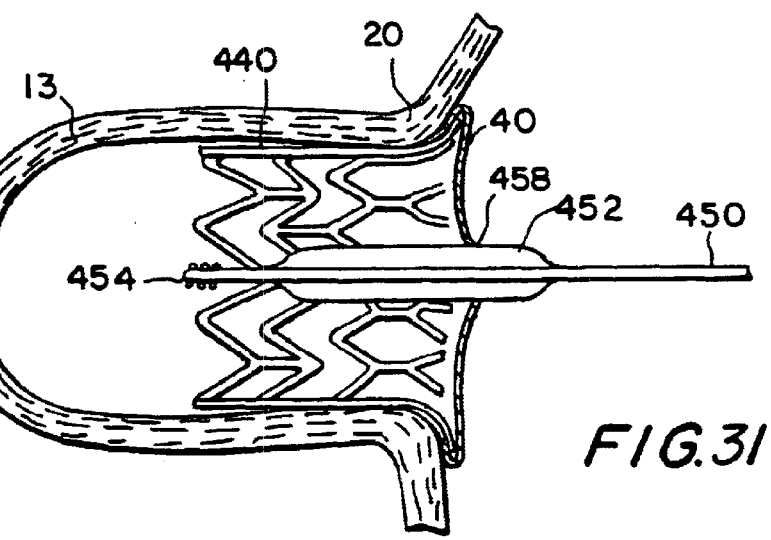
FIG. 31 is a partial cross-sectional view similar to FIG. 30 illustrating a still later stage in the procedure in accordance with the invention.

FIGS. 29–31 illustrate the procedure for installing attachment apparatus 440 and membrane 40 in the atrial appendage 13. In an initial step (FIG. 29), balloon structure 452, along with attachment apparatus 440 are inserted into the atrial appendage 13 in its initial, compact configuration. In FIG. 30, expansion fluid is passed through catheter 450 and exits through port 453 to fill the interior of balloon structure 452. Balloon structure 452 expands, thereby radially enlarging attachment apparatus 440, as described with respect to FIGS. 21–24, above. In a preferred embodiment, proximal portion 455 of balloon 452 is constructed to expand to a greater extent in order to deflect members 471 radially outward. Alternatively, members 471 may be constructed to expand to a greater extent than the rest of the attachment member 440 when expanded by balloon 452. In another embodiment, members 471 may be fabricated from a self-expanding material, such as, e.g., nitinol, wherein members 471 are normally biased in the radially outward configuration. Consequently, the outer periphery of membrane 40 is expanded to be in direct contact with the atrial wall surrounding the ostium 20. Members 471 provide additional support to provide a good seal with the edge of the membrane 40.

As illustrated in FIG. 31, attachment apparatus 440 engages the interior of the atrial appendage 13, thereby securing the membrane 40 in position across the ostium 20, such that the outer periphery of membrane 40 is in direct engagement with the atrial wall surrounding the ostium 20. Balloon structure 452 may be removed from the atrial appendage 13 by returning the balloon structure 452 to its initial compact configuration (e.g., by draining the expansion fluid therefrom) and withdrawing the balloon structure proximally through opening 458. As described above with respect to FIGS. 25–28, the membrane may be fabricated with an elastic portion which expands to permit the withdrawal of the balloon structure therethrough, and which subsequently reduces in size to inhibit the passage of thrombi, clots and emboli therethrough into the atrium. The catheter structure 442 may be subsequently removed from the patient. Alternatively, the balloon structure 452 may remain within the atrial appendage 13 following expansion of attachment apparatus 440 and subsequent return of the balloon structure 452 to its initial compact configuration. For example, catheter 450 may be detachable from balloon structure 452 in a manner similar to the configuration of catheter 410 and tube 404 (FIG. 16). Alternatively, attachment structure 440 may be manufactured from a self-expanding material, such as nitinol, wherein attachment structure is normally biased in a configuration such as that shown in FIG. 24. In order to install the attachment structure 440 within the atrial appendage 13, the attachment structure 440 may be constrained in a tube. The attachment structure 440 may subsequently be deployed from the tube and permitted to self-expand to a configuration similar to that shown in FIG. 31.

Figure 32:
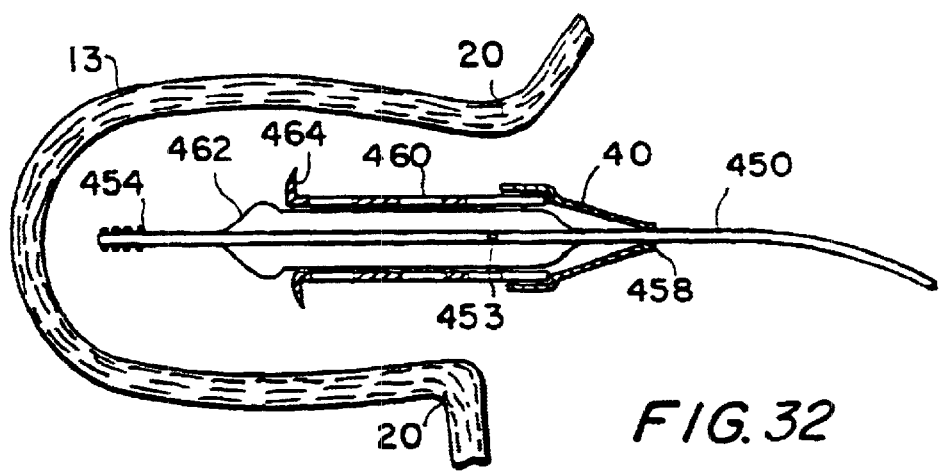
FIG. 32 is a view similar to FIG. 31 illustrating an alternative embodiment of the apparatus illustrated in FIGS. 19–23.
Figure 33:
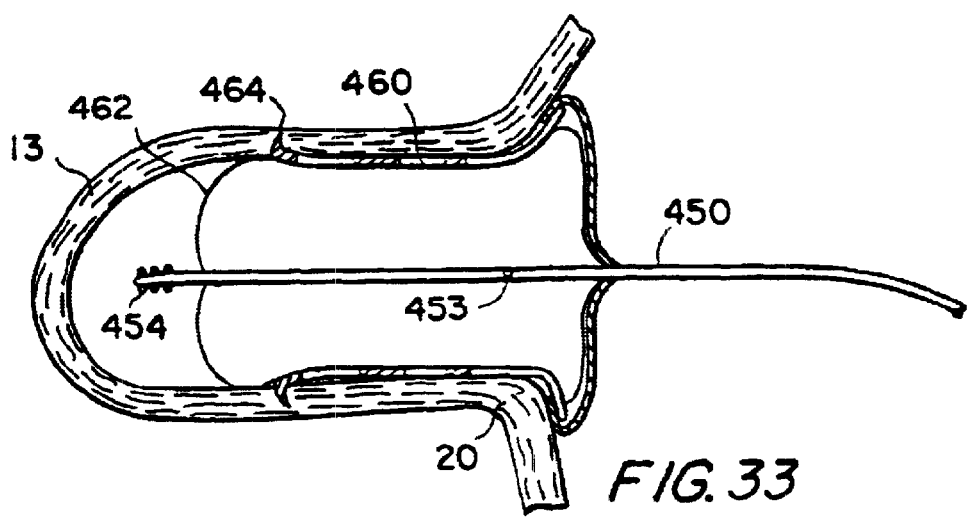
FIG. 33 is a partial cross-sectional view similar to FIG. 32 illustrating a later stage in the procedure in accordance with the invention.
Figure 34:
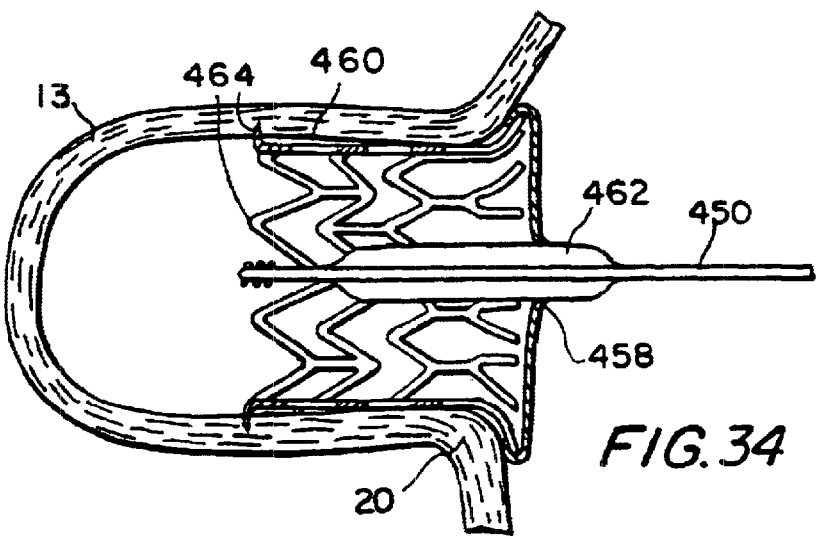
FIG. 34 is a partial cross-sectional view similar to FIG. 33 illustrating a still later stage in the procedure in accordance with the invention.

FIGS. 32–34 illustrate another embodiment of the invention. Attachment apparatus 460 and balloon apparatus 462 are substantially the same as attachment apparatus 440 and balloon apparatus 452, described hereinabove, with the differences noted below. Attachment apparatus 460 may be provided with a plurality of engagement members 464, such as prongs, hooks, or the like, in order to engage and/or pierce the wall of the atrial appendage to provide additional securement of the attachment apparatus 460. Balloon structure 452 may be used in connection with attachment apparatus 460. Alternatively, balloon structure 462 may be provided having a distal end portion which is configured to expand to a greater extent than the proximal portion thereof (FIG. 33). This greater expansion of the balloon structure 462 provides additional force in the area of the engagement members 464 to drive them into the wall of the atrial appendage 13 (FIG. 34).

Figure 35:
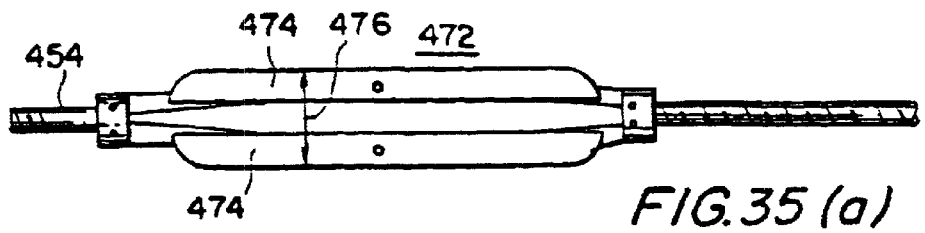
FIG. 35(a) illustrates an alternative embodiment of the apparatus illustrated in FIGS. 19–20 in accordance with the invention.
FIG. 35(b) illustrates the apparatus illustrated in FIG. 35(a) in an expanded configuration in accordance with the invention.
Figure 35:
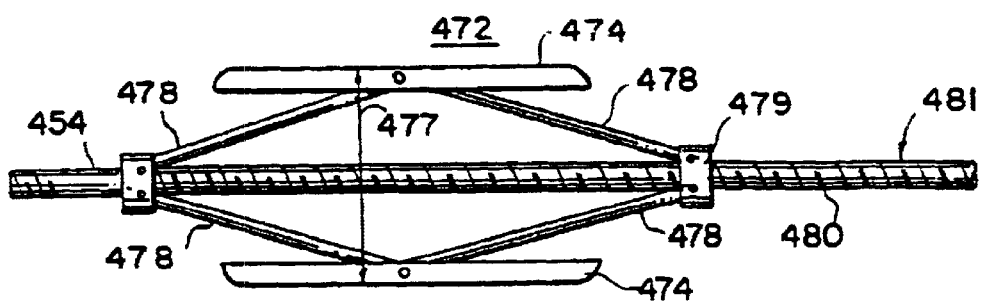
Figure 36:
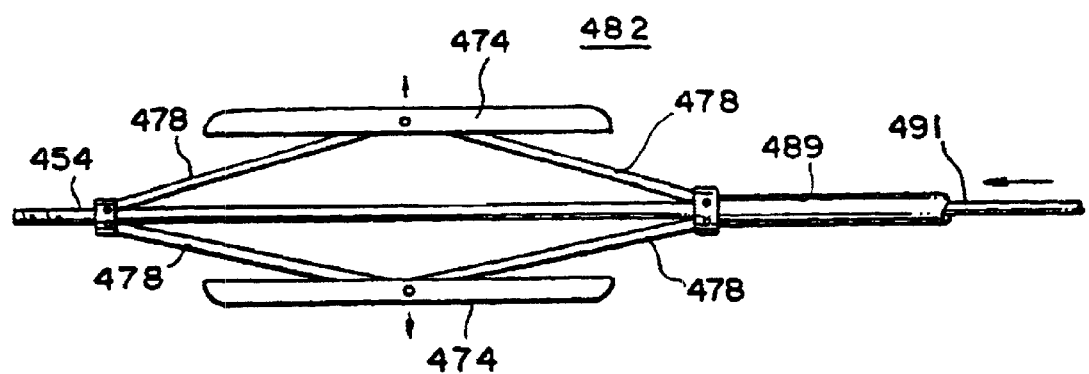
FIG. 36 is a view similar to FIG. 35(b) illustrating another embodiment in accordance with the invention

FIGS. 35–36 illustrate additional embodiments of expandable structures for radially enlarging the attachment apparatus 440 (or 460) within the atrial appendage. Instead of, or in addition to balloon structures (such as balloon structure 452), it is also contemplated that mechanical expansion structures may be particularly useful. FIGS. 35(a)–(b) illustrate a mechanical expansion structure 472 which may be used to radially expand attachment apparatus 440. As shown in FIG. 35(a), mechanical expansion structure 472 may have a compact configuration wherein a plurality of contact members 474 define a diameter 476 that enables the structure to be inserted within the attachment apparatus 440. As illustrated in FIG. 35(b), mechanical expansion structure 472 also has an expanded configuration, wherein contact members 474 are further spaced apart to define a larger diameter 477 which radially enlarges the attachment apparatus to the configuration illustrated in FIGS. 21–24 and 30–31. A linkage configuration may include linkage members 478 and sleeve 479. Sleeve 479 is provided with internal threading (not shown) which engages external threading 480 on a portion of drive screw 481. Angular rotation of drive screw 481 (as indicated by the arrow) provides longitudinal movement of sleeve 479 which cooperates with linkage members 478 to controllably move the contact members 474 between the compact and expanded configurations.

FIG. 36 illustrates mechanical expansion structure 482, which is substantially identical to mechanical expansion structure 472. Sleeve 489 interacts with linkage members 478 to controllably move contact members 474, as described above with respect to sleeve 479. Sleeve 489 is longitudinally slidable with respect to elongated member 491. A locking structure (not shown) may also be provided to fix the position of sleeve 489 (and thus contact members 474) with respect to elongated member 491.

Mechanical expansion structures 472 and 482 may remain in the atrial appendage 13 following the expansion of attachment apparatus 440 (or 460). A portion of the drive screw 481 or elongated member 491 may be detachable from the expansion structures 472 or 482, respectively (not shown). Alternatively, apparatus substantially similar to mechanical expansion structures 472/482 may be useful as supporting structures for membrane 40. According to this embodiment, membrane 40 may be attached to an end portion of structure 472/482, e.g., by attaching membrane 40 to end portions of contact members 474 or by substantially enclosing contact members 474 and linkage members 478. The structure 472/482 may be positioned in the atrial appendage 13 and expanded as described above, such that membrane 40 extends across the ostium 20 to allow blood to pass therethrough while inhibiting the passage of thrombus through the membrane 40. Drive screw 481 or elongated member 491 may be subsequently detached from the apparatus 472/482.

FIGS. 37–39 illustrate another embodiment of the invention. Membrane 40 may be installed in the atrial appendage 13 and held therein by attachment apparatus 500, which preferably consists of a pair of flexible wire portions 502a and 502b, which are preferably constructed of a material such as nitinol or Elgiloy or stainless steel and having a wire diameter of approximately 0.005 to 0.020 inch. Each wire portion 502a/502b may include a curved portion 504a/504b, a pair of support members 506a/506b and a plurality of engagement members 508. The curved portions 504a/504b define a substantially closed portion for mounting the membrane 40. The membrane 40 is attached with sutures, adhesive, or other appropriate means. The engagement members 508 are configured to engage the interior of the atrial appendage 13 to secure the membrane 40 in position across the ostium 20, as will be described herein. The engagement members 508 may be provided with atraumatic end portions 510.

FIG. 40 illustrates attachment apparatus 500 and membrane 40 in a compacted configuration for installation in the atrial appendage 13. Preferably, a delivery catheter apparatus 520 is used to introduce the attachment apparatus 500 and membrane 40 to the atrial appendage. The curved portions 504a/504b are deflected proximally toward parallelism with the longitudinal axis of the catheter 520, and the engagement members 508 are deflected distally toward parallelism with the longitudinal axis. An inner member 522 is slidably received within the interior of catheter 520 and may be moved relatively longitudinally with respect to catheter apparatus 520 in order to deploy and install the attachment apparatus 500 and membrane 40.

Figure 41:
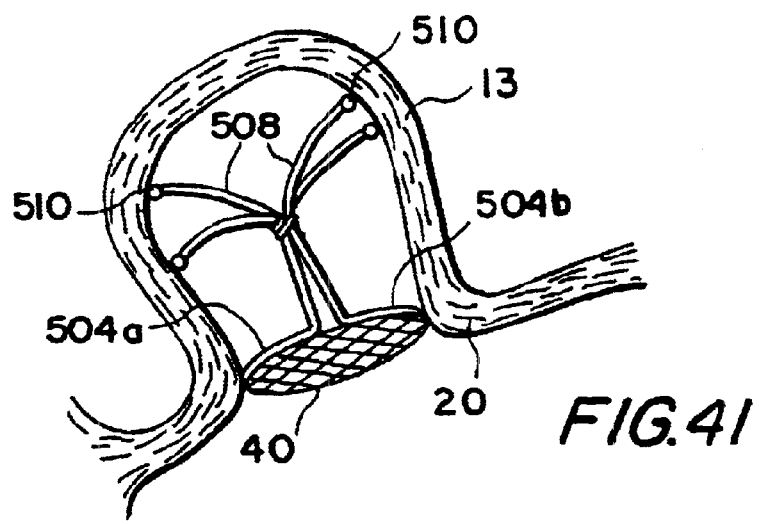
FIG. 41 is a partial cross-sectional view illustrating a first installed configuration of the apparatus of FIGS. 37–39 in accordance with the invention.
Figure 42:
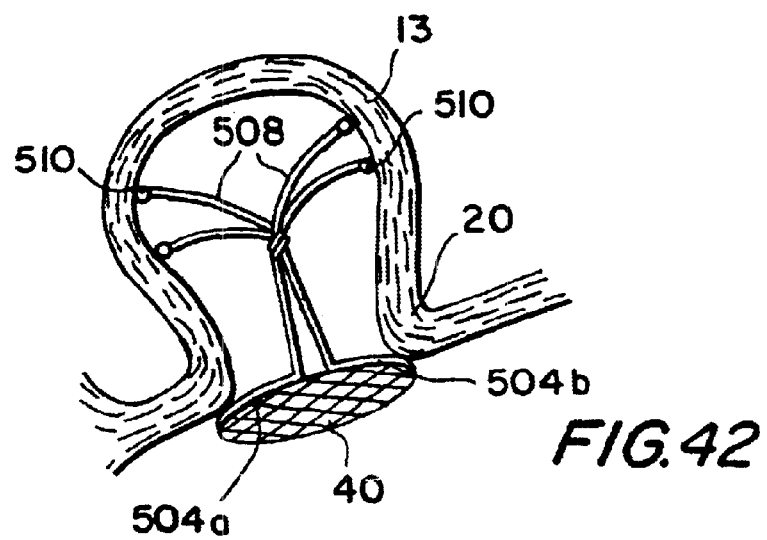
FIG. 42 is a partial cross-sectional view similar to FIG. 41 illustrating a second installed configuration of the apparatus of FIGS. 37–39 in accordance with the invention.
Figure 43:
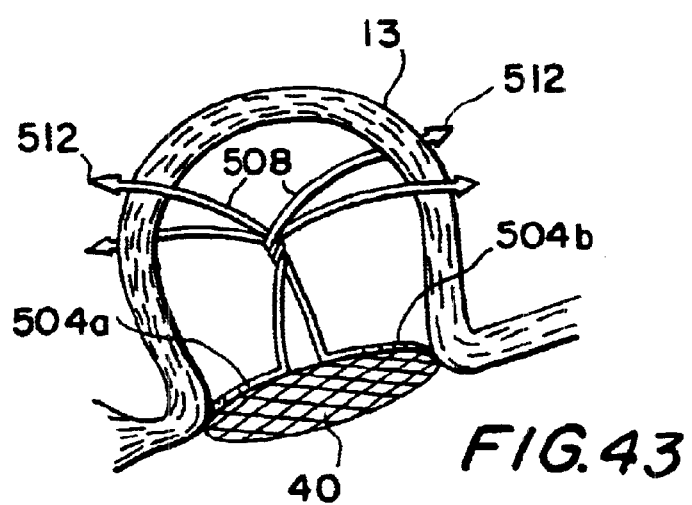
FIG. 43 is a partial cross-sectional view illustrating another embodiment of the apparatus in accordance with the invention.
Figure 50:
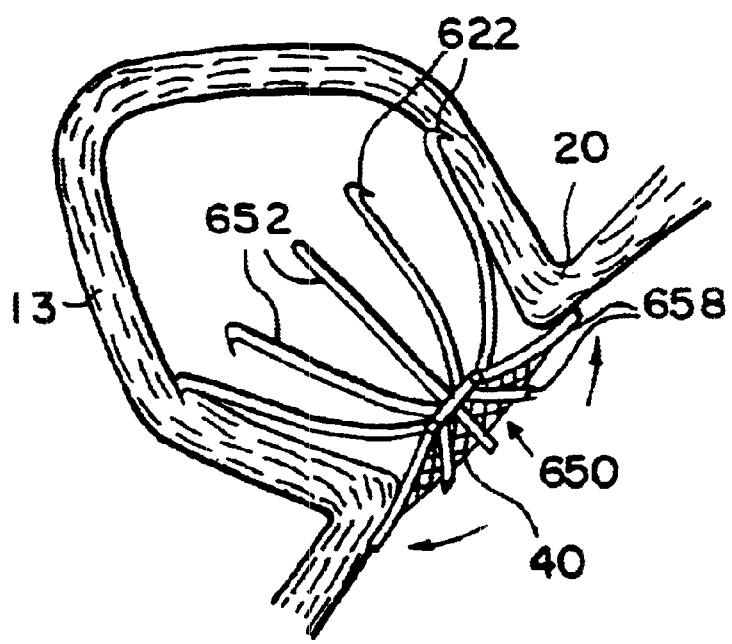
FIG. 50 is a partial cross-sectional view similar to FIG. 49 illustrating a later stage in the procedure in accordance with the invention.

FIGS. 41–43 illustrated several options for installing the membrane across the ostium 20. As illustrated in FIG. 50, the curved portions 504a/504b are positioned within the walls of the ostium 20 itself. The engagement members 508 provide additional support by engaging the interior of the atrial appendage. Alternatively, the curved portions 504a/504b are positioned outside the ostium within the atrium. Engagement members 508 retain the outer periphery of membrane 40 in direct engagement with the atrial wall surrounding the ostium 20. According to yet another alternative embodiment, engagement member 508 are provided with sharpened barb end portions 512 which engage and/or pierce the wall of the atrial appendage to secure the membrane in position (FIG. 43).

FIGS. 44–45 illustrate another embodiment of the invention. Attachment apparatus 650 provides a first plurality of strut wires 652 that extend distally and radially outward from a support ring 654 toward the distal end portion 656 of the attachment apparatus 650, and a second plurality of strut wires 658 that extend proximally and radially outward from support ring 654 toward the proximal end portion 660. The strut wires 652/658 may be constructed from an alloy, such as nitinol, having shape memory characteristics. The support ring 654 maintains the strut wires 652/658 in the proper configuration and may be made of radiopaque materials, such as, e.g., platinum to provide fluoroscopic imaging of the device position. The strut wires 652 may be provided with barbs 662 or other methods for attachment to the interior of the atrial appendage. The struts 652/658 are configured to engage the walls of the ostium on the inner and outside sides thereof, respectively.

The strut wires 658 may serve as a membrane mounting structure. The membrane 40 is attached to strut wires 658 and provides the characteristics described above. In one embodiment, the membrane 40 is permeable wherein blood is allowed to pass through the membrane 40, but thrombi, clots, and emboli are inhibited from passing therethrough. Alternatively, the membrane 40 may be impermeable to the flow of thrombus as well as blood. The membrane 40 may be connected to the strut wires 602 using adhesive, sutures, encapsulation or other means.

Another embodiment of the invention is illustrated in FIG. 46. Attachment apparatus 670 is constructed of braided or woven mesh material rather than the strut wires 652/658 described with respect to FIGS. 44–45. The distal portion 672 is configured to engage the wall of the atrial appendage adjacent the inner portion of the ostium, and the proximal portion 676 is configured to engage the outer portion of the ostium, and the neck portion 674 is disposed therebetween. The braided or woven self-expanded mesh material of attachment apparatus 670 has similar filtering characteristics as membrane 40, or alternatively, a membrane is attached to the mesh material to provide those characteristics.

FIGS. 47–48 illustrate apparatus for delivering and installing the attachment apparatus 650 and membrane 40 and/or attachment apparatus 670. The catheter apparatus 620 includes an outer sheath 622 and an inner member 624 slidably received within the interior of outer sheath 622. The outer sheath 622 and inner member 624 may be fabricated from materials, such as polymers, that are sufficiently flexible to negotiate the anatomy, yet sufficiently rigid for relative longitudinal movement to deploy and position the attachment apparatus 600. Inner member 624 may have a distal end portion 626 and a shoulder portion 628. Strut wires 652 of apparatus 650 (or distal portions 672 of apparatus 670) are deflected distally toward parallelism with the longitudinal axis of the catheter device 620 and retained in the deflected configuration by the outer sheath 622. Similarly, strut wires 658 (or proximal portions 676) are deflected proximally toward parallelism with the longitudinal axis and retained in this configuration by the outer sheath 622. In order to deploy the attachment apparatus 600, the outer sheath 622 is moved longitudinally relative to the inner member 626. The shoulder portion 628 retains the attachment apparatus 650/670 in position. Upon retraction of the outer sheath 622, the shape memory characteristics of the strut wires 652/658 (or portions 672/676) cause the apparatus to return to a shape approximating that of FIG. 44 (or FIG. 46).

Figure 49:
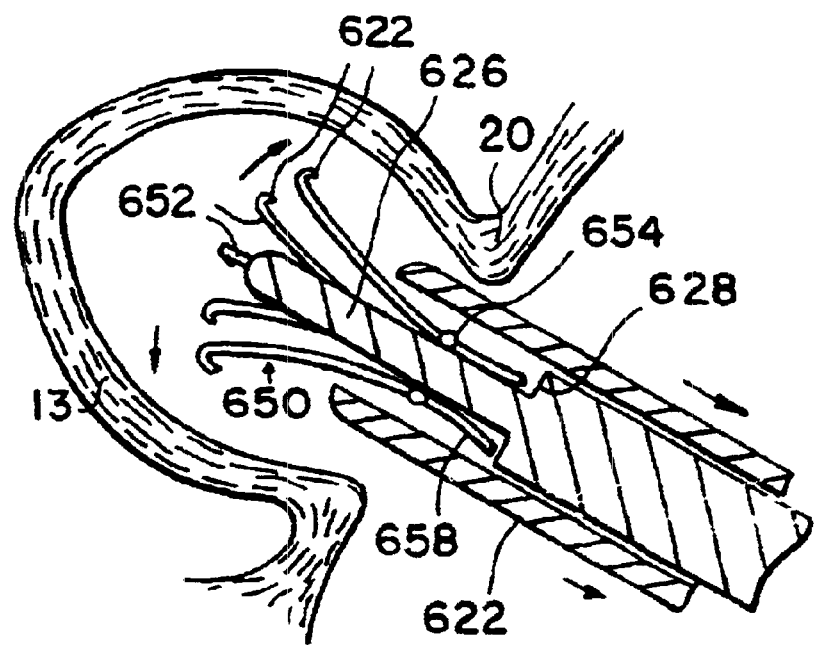
FIG. 49 is a partial cross-sectional view of the apparatus of FIGS. 44–45 illustrating an early stage in the procedure in accordance with the invention.

FIGS. 49–50 illustrate the installation of attachment apparatus 650/670 and membrane 40 in greater detail. As illustrated in FIG. 49, the catheter device 622 is advanced partially within the atrial appendage 13. The outer sheath 622 may be retracted proximally, which permits the strut wires 652 to extend radially outwardly. The physician may use the radiopaque characteristics of the ring 654 in order to properly position the ring 654 within the ostium 20. Further proximal retraction of the outer sheath 622 allows the distal strut wires 652 and the proximal strut wires 658 to extend radially outward and engage the interior of the atrial appendage 13 (FIG. 50). The barbs 662 may engage and/or pierce the wall of the atrial appendage to provide increased stability of the attachment apparatus 600. The membrane 40 is consequently positioned across the ostium 20 such that the outer periphery of membrane 40 is secured in direct engagement with the atrial wall surrounding the ostium. In one embodiment, the membrane 40 is impermeable and does not permit blood or thrombus to flow, whereas a filtering membrane may be used to allow blood to pass through the membrane, while substantially inhibiting thrombi, clots, and emboli from exiting the atrial appendage 13. Struts 658 provide additional securement in order to maintain a leak-proof seal between membrane 40 and the atrial wall surrounding the ostium 20.

Figure 51:
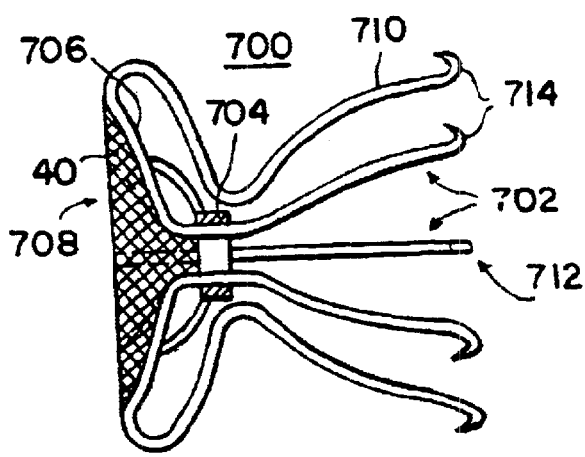
FIG. 51 illustrates yet another embodiment of the apparatus in accordance with the invention.
Figure 52:
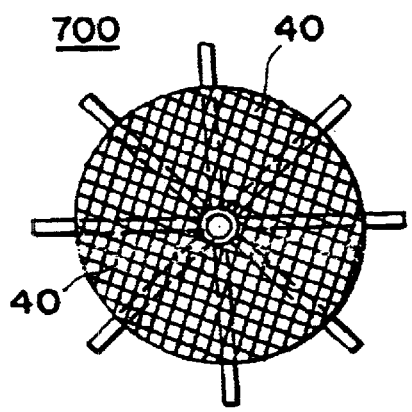
FIG. 52 is an end view of the apparatus of FIG. 51 in accordance with the invention.

FIGS. 51–52 illustrate yet another embodiment of the invention. Attachment apparatus 700 provides a plurality of strut wires 702 that extend radially outward from a support ring 704. A first portion 706 of each strut wire 702 extends towards the proximal end portion 708 of the attachment apparatus 700, and a second portion 710 of each strut wire 702 extends towards the distal end portion 712. The distal portion 710 of each strut wire 702 may be provided with a sharpened barb tip 714 or other methods for attachment to the interior of the atrial appendage. The strut wires 702 are constructed from an alloy, similar to material used for strut wires 602, above. The support ring 704 maintains the strut wires 702 in the proper configuration and is substantially similar to support ring 604, above. The proximal portions 706 and distal portions 710 of strut wires 702 are configured to engage the walls of the ostium on the outer and inner sides thereof, respectively.

The membrane 40 is attached to proximal portions 706 of strut wires 702 and may provides the filtering characteristic described above, wherein blood is allowed to pass through the membrane 40, but thrombi, clots, and emboli are inhibited from passing therethrough. Alternatively, membrane 40 may be impermeable to both blood and thrombi. The membrane 40 may be connected to the strut wires 702 using adhesive, sutures, encapsulation or other means.

Figure 53:
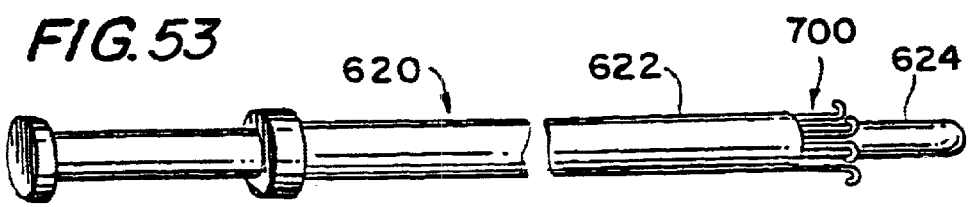
FIG. 53 illustrates additional apparatus for use with the apparatus of FIGS. 51–52 in accordance with the invention.
Figure 54:
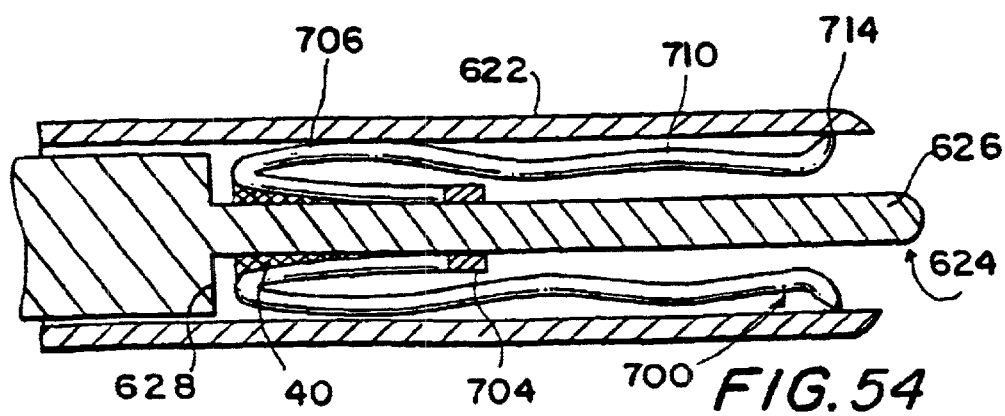
FIG. 54 is an enlarged sectional view of the apparatus of FIGS. 51 and 53 in accordance with the invention.

FIGS. 53–54 illustrate apparatus for delivering and installing the attachment apparatus 700 and membrane 40. The catheter apparatus 620 is described above with respect to FIGS. 47–48. Strut wires 702 are deflected towards parallelism with the longitudinal axis of the catheter device 620 and retained in the deflected configuration by the outer sheath 622. In order to deploy the attachment apparatus 700, the outer sheath 622 is moved longitudinally relative to the inner member 626. The shoulder portion 628 retains the attachment apparatus 700 in position. Upon retraction of the outer sheath 622, the shape memory characteristics of the strut wires 702 causes the apparatus to resume the shape approximating that of FIG. 51.

Figure 55:
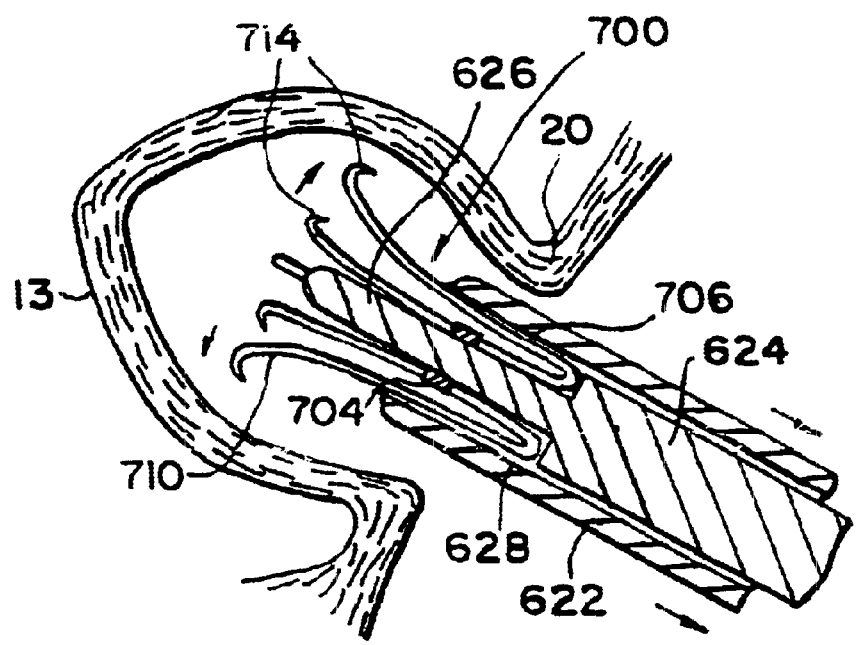
FIG. 55 is a partial cross-sectional view of the apparatus of FIG. 51 illustrating an early stage in the procedure in accordance with the invention.
Figure 56:
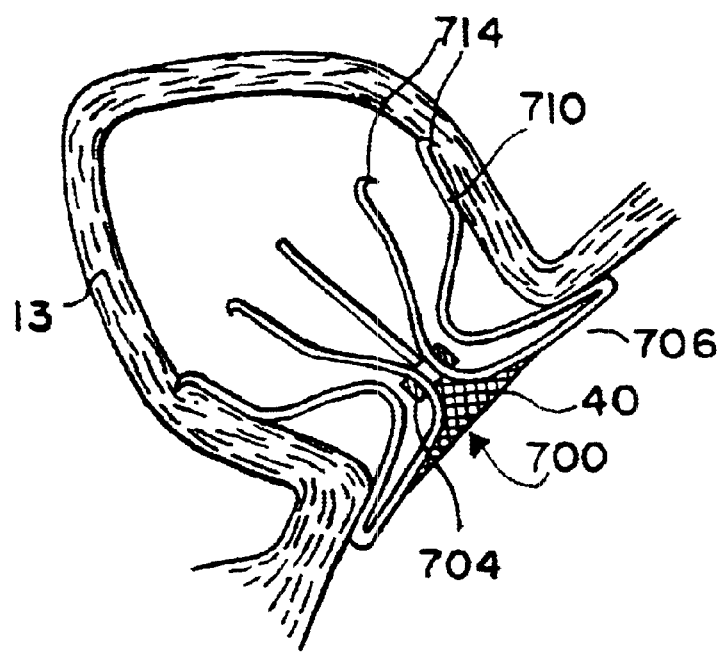
FIG. 56 is a partial cross-sectional view similar to FIG. 55 illustrating a later stage in the procedure in accordance with the invention.

FIGS. 55–56 illustrate the installation of attachment apparatus 700 and membrane 40 in greater detail. As illustrated in FIG. 55, the catheter device 622 is advanced partially within the atrial appendage 13. The outer sheath 622 may be retracted proximally, which permits the distal portions 710 of strut wires 702 to extend radially outwardly. Further proximal retraction of the outer sheath 622 allows the distal portions 710 to engage the interior of the atrial appendage 13 and the proximal portions 706 to engage the outer portion of the ostium 20 (FIG. 56). Struts 706 provide additional securement in order to maintain a leakproof seal between membrane 40 and the atrial wall surrounding the ostium 20. The barbs 714 may engage and/or pierce the wall of the atrial appendage to provide increased stability of the attachment apparatus 700. The membrane 40 is consequently positioned across the ostium 20, such that the outer periphery of the membrane is secured in direct engagement with the atrial wall surrounding the ostium 20. Struts 706 provide additional securement of the membrane to the atrial wall to provide a leakproof seal. A court order should be obtained in order to allow blood to pass through the membrane, while substantially inhibiting thrombi, clots, and emboli from exiting the atrial appendage 13.

Figure 57:
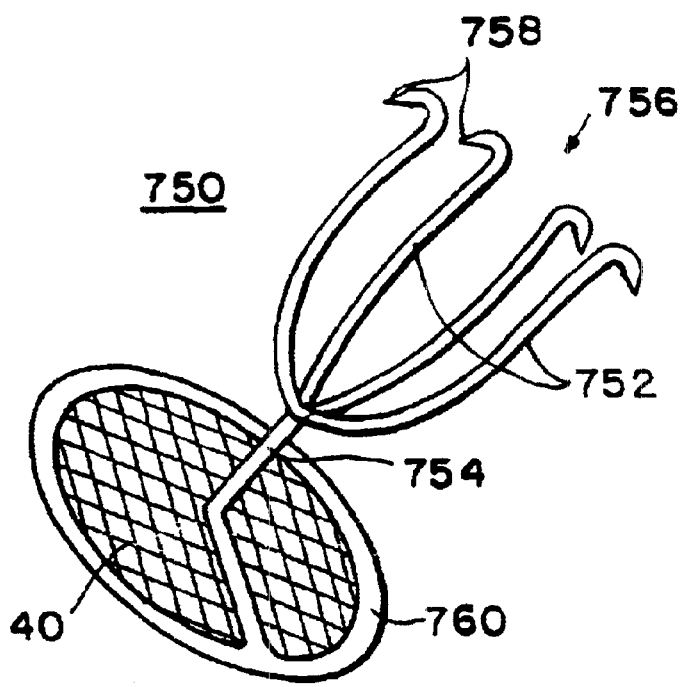
FIG. 57 illustrates another embodiment of the apparatus in accordance with the invention.
Figure 58:
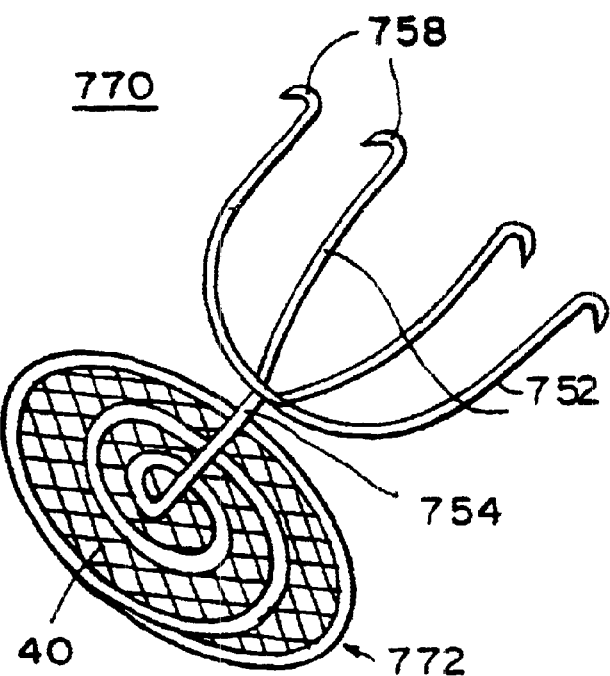
FIG. 58 illustrates yet another embodiment of the apparatus in accordance with the invention.

FIGS. 57–58 illustrate additional embodiments of the invention. Attachment apparatus 750 includes a plurality of strut wires 752 that extend radially outward and distally from a support member 754 towards the distal end portion 756. Each strut wire 752 may be provided with a sharpened barb tip 758 or other methods for attachment to the interior of the atrial appendage. The strut wires 702 are constructed from an alloy, similar to the material used for strut wires 602, above. The support member 754 maintains the strut wires 752 in the desired configuration.

The proximal end portion of support member 754 supports a curved membrane mounting structure 760 that defines a substantially closed curve. The membrane 40 is attached to membrane mounting structure 760 and may provide the filtering characteristic described above, wherein blood is allowed to pass through the membrane 40, but thrombi, clots, and emboli are inhibited from passing therethrough. The membrane 40 may alternatively be impermeable to blood flow and the passage of thrombi. The membrane 40 may be connected to the membrane mounting structure 760 using adhesive, sutures, encapsulation or other means.

The attachment apparatus 770, illustrated in FIG. 58 is substantially identical to attachment apparatus 750, with the differences noted herein. For example, the proximal end portion of support member 754 supports a membrane mounting structure 772 having a spiral configuration. The membrane 40 is attached to spiral mounting structure 772 substantially as described above with respect to membrane mounting structure 760, above. The spiral configuration may, e.g., assist in reducing the mounting structure to a compacted configuration during installation.

Figure 59:
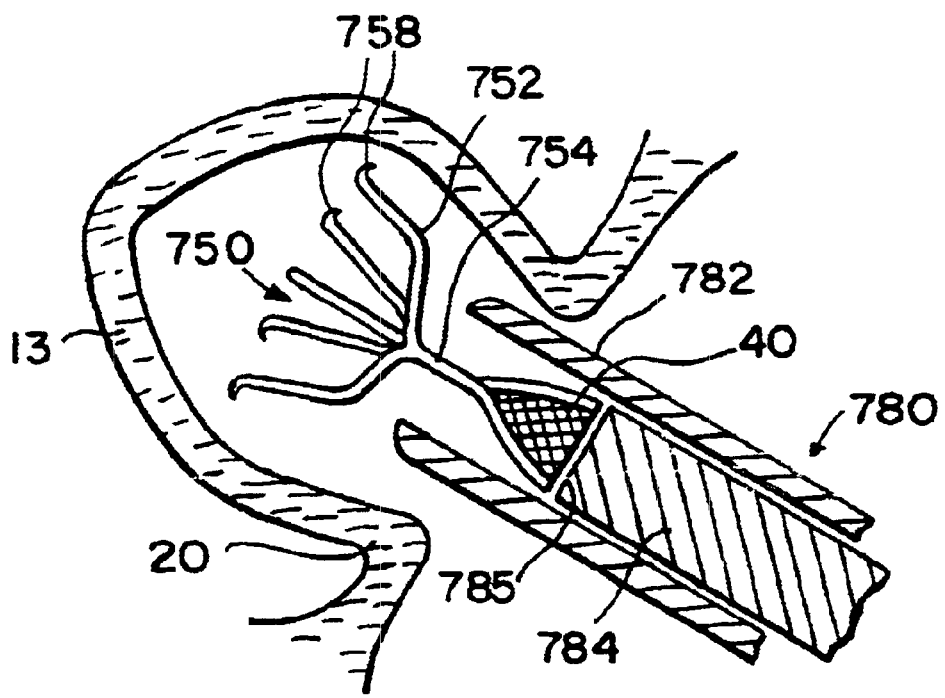
FIG. 59 is a partial cross-sectional view of the apparatus of FIG. 57 illustrating an early stage in the procedure in accordance with the invention.
Figure 60:
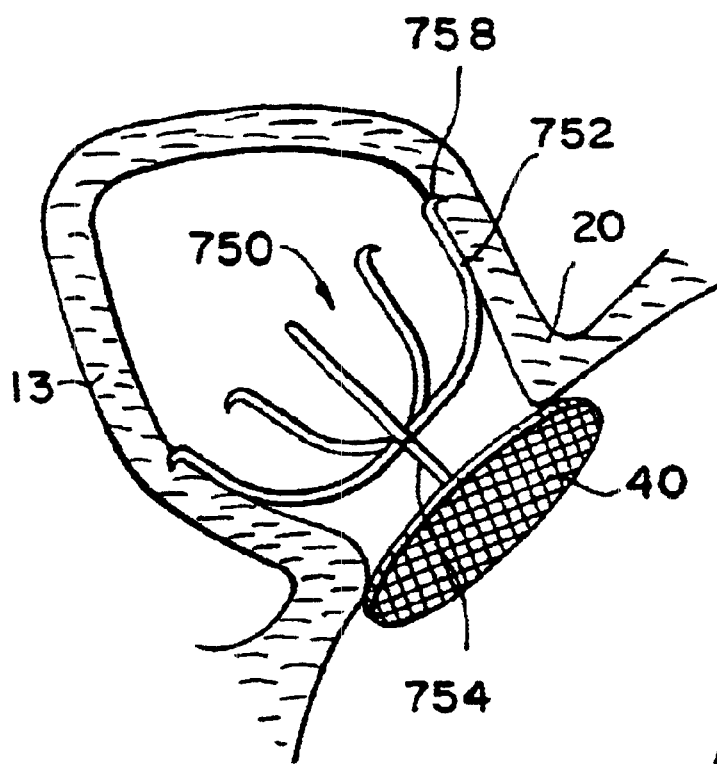
FIG. 60 is a partial cross-sectional view similar to FIG. 59 illustrating a later stage in the procedure in accordance with the invention.

FIGS. 59–60 illustrate the installation of attachment apparatus 750 (or 770) and membrane 40 in the atrial appendage 13. Catheter apparatus 780 is provided for delivering and installing the attachment apparatus 750 and membrane 40. The catheter apparatus 780 is similar to catheter apparatus 620 described above with respect to FIG. 55. Catheter apparatus 780 includes an outer sheath 782 and an inner member 784. Inner member 784 preferably has an engagement surface 785 on a distal end portion thereof. During installation, strut wires 752 are deflected towards parallelism with the longitudinal axis of the catheter device 780 and retained in the deflected configuration by the outer sheath 782 (not shown in FIG. 59). Similarly, the membrane mounting portion 760 (or 772) is folded, rolled or otherwise compacted inside outer sheath 782 as illustrated in FIG. 59.

In order to deploy the attachment apparatus 750, the catheter device 780 is advanced partially within the atrial appendage 13. The outer sheath 782 may be retracted proximally, which permits the strut wires 752 to extend radially outwardly due to its shape memory characteristics, as shown. The inner member 784 retains the attachment apparatus 750 in position.

As illustrated in FIG. 60, further proximal retraction of the outer sheath 782 allows the strut wires 752 to extend radially outward and engage the interior of the atrial appendage. The barbs 758 may engage and/or pierce the wall of the atrial appendage to provide increased stability of the attachment apparatus 700. The membrane mounting structure 760 (or 772) is likewise permitted to return to its disc-like configuration, such that membrane 40 is positioned across the ostium 20 such that the outer periphery of the membrane 40 is secured in direct engagement with the atrial wall surrounding the ostium. The membrane 40 may be permeable in order to allow blood to pass through the membrane, while substantially inhibiting thrombi, clots, and emboli from exiting the atrial appendage 13. Alternatively, the membrane 40 may be impermeable to blood flow and the passage of thrombus.

FIGS. 61–67 illustrate additional embodiments of the invention wherein membrane 40 is sized to cover the ostium 20 of the atrial appendage and secured in direct engagement with the atrial wall surrounding the ostium. Membrane 40 is thus provided with a diameter or other dimension that is larger than the diameter or corresponding dimension of the ostium 20 in order to entirely cover the ostium. More particularly, membrane 40 defines an outer periphery which is secured in direct engagement with the ostium or the atrial wall surrounding the ostium.

Figure 61:
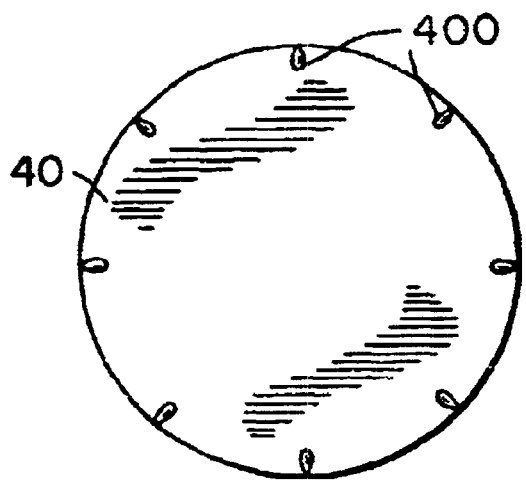
FIG. 61 is a simplified elevational view of another embodiment of the membrane in accordance with the invention.
Figure 62:
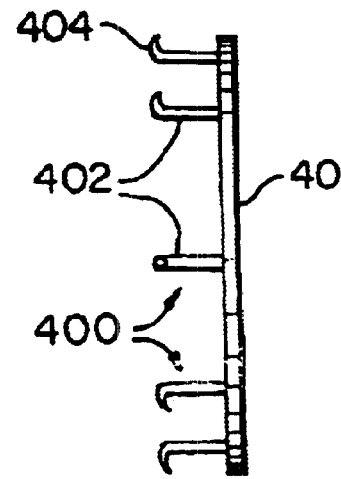
FIG. 62 is a side view of the membrane taken from direction 62 of FIG. 61, in accordance with the invention.

As illustrated in FIGS. 61–62, membrane 40 is provided with a plurality of engagement members 400, which may be attached to and positioned about the outer periphery of membrane 40, and which may have shank portions 402 and barbed free ends 404 which in this case may extend radially outward from the engagement members 400.

Figure 63:
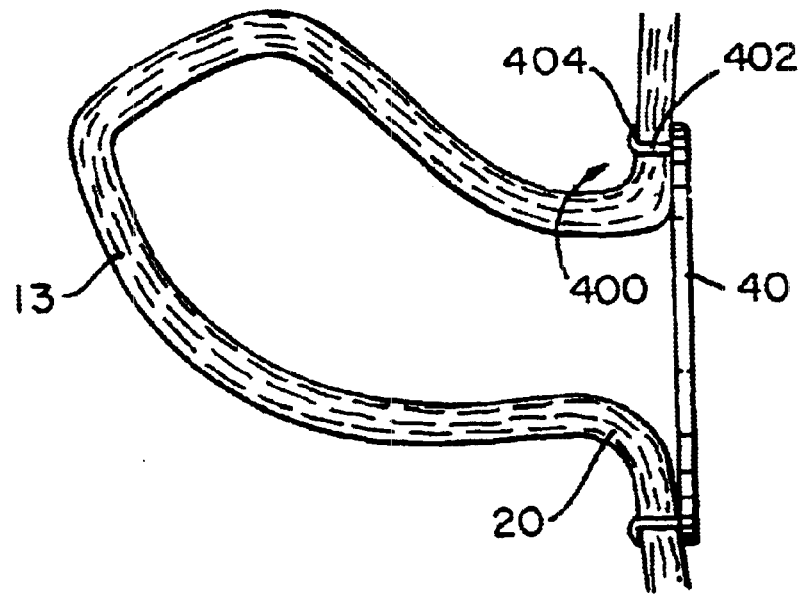
FIG. 63 is view in partial section of the membrane of FIGS. 61–62 illustrating a typical use in accordance with the invention.

As shown in FIG. 63, membrane 40 is installed to cover ostium 20. Engagement members 400 pierce the wall of the ostium 20 or the atrial wall surrounding the ostium to attach the membrane 40 directly to the ostium 20 or the atrial wall surrounding the ostium. Barbed free ends 404 prevent the engagement members 400 from being withdrawn from the wall, and assists in securing the membrane 40 in position as shown in the FIG. Membrane 40 has a structure which blocks thrombus from leaving the atrial appendage and entering the bloodstream. A filtering permeable membrane may alternatively be used, which allows blood to flow through while substantially inhibiting thrombus.

Figure 64:
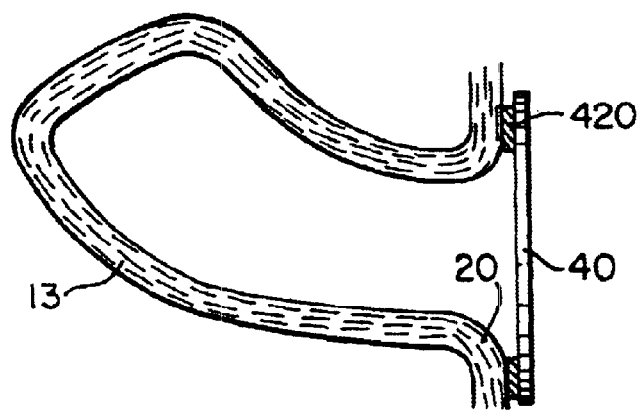
FIG. 64 is view in partial section of the yet another embodiment of the membrane, illustrating a typical use in accordance with the invention.

FIG. 64 illustrates another embodiment wherein the membrane 40 covers the ostium 20 of the atrial appendage 13. A biocompatible tissue adhesive 420, such as fibrin glue or cyanoacrylate or a similar material, may be applied about the outer periphery of the membrane and used to attach the membrane 40 directly to the ostium 20 or the wall of the atrium surrounding the ostium 20. Membrane 40 blocks thrombus from leaving the atrial appendage and entering the bloodstream. A filtering permeable membrane may alternatively be used, which allows blood to flow through while substantially inhibiting thrombus.

Figure 65:
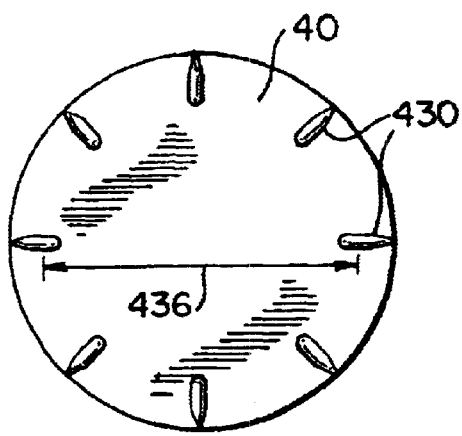
FIG. 65 is a simplified elevational view of still another embodiment of the membrane in accordance with the invention.
Figure 66:
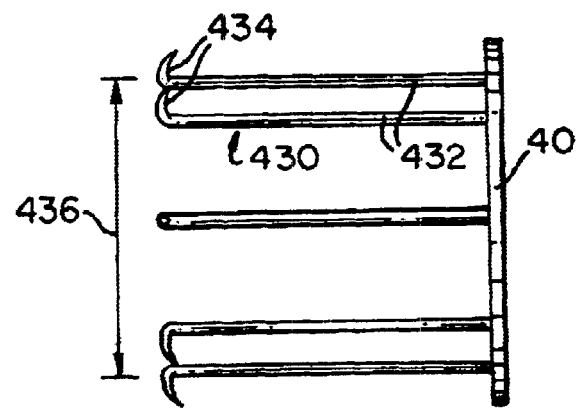
FIG. 66 is a side view of the membrane taken from direction 66 of FIG. 65, in accordance with the invention.

FIGS. 65–66 illustrate still another embodiment of the invention wherein membrane 40 is provided with a plurality of engagement members 430. Each of engagement members 430 is mounted about the periphery of membrane 40, and has an elongated shank portion 432 that extends distally longitudinally and a barbed free end 434 that may extend radially outward from the elongated shank portion 432. Shank portion 432 is substantially longer than shank portions 402 described above with respect to FIGS. 61–63. Engagement members 430 define a spacing 436, or the distance between opposite engagement members 430, exclusive of the radial projection of the barb-like free ends 434, that is similar in size to the interior dimensions of the ostium 20. This spacing 436 between engagement members 430 located on opposite sides of the membrane 40 provides the feature of centering the engagement members within the interior of the ostium 20 and the atrial appendage 13.

Figure 67:
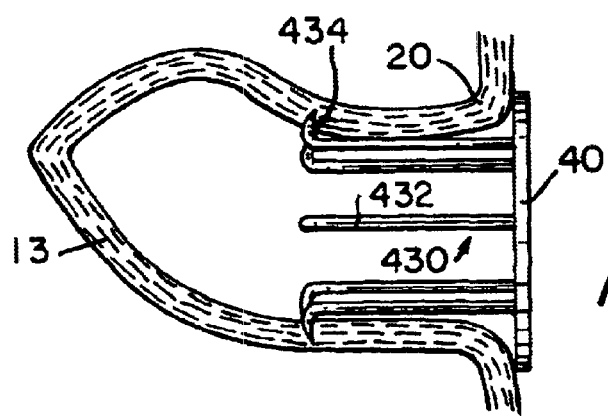
FIG. 67 is view in partial section of the membrane of FIGS. 65–66 illustrating a typical use in accordance with the invention.

As shown in FIG. 67, membrane 40 is installed to cover ostium 20. Elongated shank portions 432 extend a distance into the ostium 20 or the atrial appendage 13 and assist in centering the membrane 40 within the ostium 20. Barbed free ends 434 engage the interior wall of the atrial appendage 13 to prevent the engagement members 430 from being withdrawn from the wall, and secure the membrane 40 in direct engagement with the ostium 40 or the atrial wall surrounding the ostium 40 as shown in the FIG. Membrane 40 has a structure which blocks thrombus from leaving the atrial appendage and entering the bloodstream. A filtering permeable membrane may alternatively be used, which allows blood to flow through while substantially inhibiting thrombus.

The devices described above may be percutaneously delivered to the left and right atrial appendages 13, 23 respectively. The devices may have materials in them which enhance visualization or imaging by ultrasound, x-ray or other means making it easier for the device to be implanted and accurately centered with respect to the ostium 20 of the atrial appendage 13. This may consist of small beads placed strategically on the membrane, the connecting elements, or on the anchors. Referring to FIG. 1 catheter 21 is seen entering the heart by way of the aorta 12 to the left ventricle 16 passing through the mitral valve 17 and then entering the left atrial appendage 13 to apply the membrane 40 in one of the embodiments as disclosed above. In FIG. 2 the catheter 21 enters the heart from the femoral vein, passes through the inferior vena cava 18 to the right atrium and then passes through the fossa ovalis 19 or through the septum 29 into the left atrium 11 and then approaches the left atrial appendage 13 to apply the membrane 40 thereto. FIG. 3 shows the catheter 21 being applied to the right atrial appendage 23. Catheter 21 may enter the heart through the jugular vein 28 or the femoral vein to the inferior vena cava 18.

It is understood that the invention may be practiced with numerous means of attaching the membrane 40 across the ostium 20 of the atrial appendages 13 and 23. All of the above embodiments shown and discussed for the left atrial appendage 13 are also useable on the right atrial appendage 23. Any combination of the attachment means with adhesives, prongs, cylindrical structures, anchors, disks, tethers or springs may be used. The membrane may penetrate the atrial appendage and provide a means to securely lock the membrane device into place. If permeable characteristics are preferred by the physician, other means of providing a membrane for allowing blood flow therethrough and substantially inhibiting blood clots from exiting out of the atrial appendages not listed herein may also be used.

Obviously, many modifications and variations of the present invention are possible in light of the above teachings. It is therefore to be understood that, within the scope of the appended claims, the invention may be practiced otherwise than as specifically described.

What is claimed is:

1. A method of securing a membrane over an ostium of a left atrial appendage in a patient to prevent thrombus from leaving the left atrial appendage, comprising:

providing a membrane configured to extend over the ostium of the left atrial appendage, the membrane having an outer periphery with a dimension larger than a corresponding dimension of the ostium;

positioning the membrane over the ostium such that the outer periphery is in direct contact with an atrial wall surrounding the ostium; and securing the outer periphery of the membrane in direct engagement with the atrial wall surrounding the ostium.

2. The method defined in claim 1 wherein securing the outer periphery of the membrane in direct engagement with the atrial wall surrounding the ostium comprises applying an adhesive between the outer periphery of the membrane and the atrial wall surrounding the ostium.

3. The method defined in claim 1, which further comprises:

providing a plurality of engagement members attached to the membrane at a plurality of locations about the outer periphery of the membrane, wherein securing the outer periphery of the membrane in direct engagement with the atrial wall surrounding the ostium comprises piercing the atrial wall with the engagement members.

4. The method defined in claim 3, wherein providing a plurality of engagement members comprises providing a plurality of engagement members each having an elongated shank portion extending distally from the outer periphery of the membrane and defining a spacing substantially identical to an interior dimension of the ostium, wherein securing the outer periphery of the membrane in direct engagement with the atrial wall surrounding the ostium comprises extending the elongated shank portions into the ostium.

5. The method defined in claim 4, wherein providing a plurality of engagement members comprises providing a plurality of engagement members each having a barbed portion configured to engage an interior wall of the atrial appendage, wherein securing the outer periphery of the membrane to the atrial wall surrounding the ostium comprises engaging the interior wall of the atrial appendage with the barbed portion.

6. The method defined in claim 1, which further comprises:

providing a securement structure extending distally from the membrane, wherein securing the outer periphery of the membrane in direct engagement with the atrial wall surrounding the ostium comprises inserting the securement structure into the ostium, and engaging an interior wall of the left atrial appendage with the securement structure.

7. The method defined in claim 1, wherein the securement structure is configured for annular enlargement by inflation of an expansion structure, and wherein engaging the interior wall of the left atrial appendage with the securement structure comprises enlarging the securement structure by expanding the expansion structure located in an interior of the securement structure.

8. The method defined in claim 1, wherein the securement structure is resiliently biased in a enlarged configuration for engagement with the interior wall of the left atrial appendage and may be constrained in a reduced size configuration for installation in the left atrial appendage, wherein positioning the membrane over the ostium such that the outer periphery is in direct contact with an atrial wall surrounding the ostium comprises constraining the securement structure in a reduced size, and wherein engaging the interior wall of the left atrial appendage with the securement structure comprises allowing the securement structure to resiliently enlarge to the enlarged configuration.

* * * * *